US010683316B2

(12) United States Patent
Kash et al.

(10) Patent No.: US 10,683,316 B2
(45) Date of Patent: Jun. 16, 2020

(54) SYNTHETIC CATALASE/SUPEROXIDE DISMUTASE MIMETICS AND METHODS FOR TREATING VIRAL INFECTIONS

(71) Applicants: THE UNITED STATES OF AMERICA, AS REPRESENTED BY THE SECRETARY, DEPARTMENT OF HEALTH & HUMAN SERVICES, Washington, DC (US); TRUSTEES OF BOSTON UNIVERSITY, Boston, MA (US)

(72) Inventors: John C. Kash, Potomac, MD (US); Jeffery K. Taubenberger, Springfield, VA (US); Rodney L. Levine, Rockville, MD (US); Susan Doctrow, Arlington, MA (US)

(73) Assignees: The United States of America, as represented by the Secretary, Department of Health and Human Services, Washington, DC (US); Trustees of Boston University, Boston, MA (US)

( * ) Notice: Subject to any disclaimer, the term of this patent is extended or adjusted under 35 U.S.C. 154(b) by 127 days.

(21) Appl. No.: 14/357,556

(22) PCT Filed: Nov. 9, 2012

(86) PCT No.: PCT/US2012/064383
§ 371 (c)(1),
(2) Date: May 9, 2014

(87) PCT Pub. No.: WO2013/071059
PCT Pub. Date: May 16, 2013

(65) Prior Publication Data

US 2014/0329792 A1 Nov. 6, 2014

Related U.S. Application Data

(60) Provisional application No. 61/558,137, filed on Nov. 10, 2011.

(51) Int. Cl.
*C12Q 1/70* (2006.01)
*C07F 13/00* (2006.01)

(52) U.S. Cl.
CPC .............. *C07F 13/005* (2013.01); *C12Q 1/70* (2013.01)

(58) Field of Classification Search
CPC ................................ C07F 13/005; C12Q 1/70
See application file for complete search history.

(56) References Cited

U.S. PATENT DOCUMENTS

| | | | |
|---|---|---|---|
| 6,258,585 B1 | 7/2001 | Draper | |
| 6,455,571 B1 | 9/2002 | Maring et al. | |
| 2005/0170334 A1 | 8/2005 | Mikayama et al. | |
| 2010/0267825 A1* | 10/2010 | Malfroy-Camine ... | A61K 31/28 514/492 |

FOREIGN PATENT DOCUMENTS

| | | | |
|---|---|---|---|
| JP | 2003055259 A * | 2/2003 | |
| WO | 2004052283 A2 | 6/2004 | |
| WO | 2008144441 A1 | 11/2008 | |
| WO | WO 2008144441 A1 * | 11/2008 | ............. A61K 31/44 |

OTHER PUBLICATIONS

CAS Registry No. 53177-12-1 (retrieved from SciFinder Jan. 30, 2016).*
Rosenthal et al. (J Biol Inorg Chem, 2009, 14, 979-991).*
Snelgrove et al. (Eur. J. Immunol. 2006, 36, 1364-1373).*
WHO Report on Global Surveillance of Epidemic-Prone infectionus disease—Influenza; http://www.who.int/csr/resources/publications/influenza/CSR_ISR_2000_1/en/; from 2000. (Year: 2000).*
Over Imai et al. (Cell, 133, 235-249, Apr. 18, 2008) (Year: 2008).*
Kash et al. (Free Radic Biol Med, 67, 235-247, 2014) (Year: 2014).*
Vasquez-Fernandez et al., "Influence of the geometry around the manganese ion on the peroxidase and catalase activities of Mn(III)-Schiff base complexes", Journal of Inorganic Biochemistry, vol. 105, No. 12, pp. 1538-1547 (2011).
Doctrow et al., "Salen_Manganese Complexes as Catalytic Scavengers of Hydrogen Peroxide and Cytoprotective Agents: Structure—Activity Relationship Studies", Journal of Medicinal Chemistry, vol. 45, No. 20, pp. 4549-4558 (2002).
Dessolin et al., "Selective targeting of synthetic antioxidants to mitochondria: towards a motochondrial medicine for nuerodegenerative diseases?", European Journal of Phamacology, vol. 447, pp. 155-161 (2002).
Gutteridge, J M C and Halliwell B, "Reoygenation injury and antioxidant protection: A tale of two paradoxes", (1990) Arch. Biochem. Biophys. vol. 283, No. 2, Dec. pp. 223-226.
Moncada, et al., "Biosynthesis of Nitric Oxide From L-Argainine. A pathway for the regulation of cell function and communication", (1989) Biochem. Pharmacol., vol. 38, No. 11, pp. 1709-1715.
Saran, et al., "Reaction of NO with O2. Implications for the action of endothelium-derived relaxing factor (EDRF)", (1990) Free Rad. Res. Commun., vol. 10, Nos. 4-5, pp. 221-226.
Schubert, and Kurreck, "Oligonucleotide-Based Antiviral Strategies", Handb Exp Pharmacol. (2006) vol. 173:261-287.
Stadtman, E R, "Protein Oxidation and Aging", (1992) Science vol. 257: 1220-1224.
Zhou, et al., "Effective small interfering RNAs targeting matrix and nucleocapsid protein gene inhibit influenza A virus replication in cells and mice", Antiviral Res. (2007) vol. 76; 186-93.
Zimmerman, J J, "Therapeutic Application of Oxygen Radical Scavengers", (1991) Chest 100: 189S-192S.
Beckman, et al. "Apparent hydroxyl radical production by peroxynitrite: Implications for endothelial injury from nitric oxide and superoxide", (1990) Proc. Natl. Acad. Sci. (U.S.A.) 87: 1620-1624.
Breimer, L H, "Ionizing radiation-induced mutagenesis", (1988) Brit. J. Cancer 57: 6-18.

(Continued)

*Primary Examiner* — Daniel M Podgorski
(74) *Attorney, Agent, or Firm* — Klarquist Sparman, LLP

(57) ABSTRACT

The invention provides for the treatment of disorders related to viral infection, using salen manganese compounds.

9 Claims, 2 Drawing Sheets

(56) References Cited

OTHER PUBLICATIONS

Eisenberg, et al., "Penetration of GS4071, a novel influenza neuraminidase inhibitor, into rat bronchoalveolar lining fluid following oral administration of the prodrug GS4104", Antimicrob Agents Chemother. (1997) 41:1949-1952.
Kati, et al., "In vitro characterization of A-315675, a highly potent inhibitor of A and B strain influenza virus neuraminidases and influenza virus replication", Antimicrob Agents Chemother. (2002) 46:1014-1021.
Markland, et al., "Broad-spectrum antiviral activity of the IMP dehydrogenase inhibitor VX-497: a comparison with ribavirin and demonstration of antiviral additivity with alpha interferon", Antimicrob Agents Chemother. (2000) 44:859-866.
Marletta, M A, "Nitric oxide: biosynthesis and biological significance", (1989) Trends Biochem. Sci. 14: 488-492.
Shannon, et al., "Evaluation of Carbodine, the carbocyclic analog of cytidine, and related carbocyclic analogs of pyrimidine nucleosides for antiviral activity against human influenza type A virusus", Antimicrob Agents Chemother. (1981) 20:769-776.
Shigeta, et al., "Comparative activities of several nucleoside analogs against influenza A, B, and C viruses in vitro", Antimicrob Agents Chemother. (1988) 32:906-911.
Tomassini, et al., "A novel antiviral agent which inhibits the endonuclease of influenza viruses", Antimicrob Agents Chemother. (1996) 40:1189-1193.
Zebedee, et al., "Influenza a virus $M_2$ protein: monoclonal antibody restriction of virus growth and detection of $M_2$ in virions", J. Virol. (1988) 62:2762-2772.

* cited by examiner

SYNTHETIC CATALASE/SUPEROXIDE DISMUTASE MIMETICS AND METHODS FOR TREATING VIRAL INFECTIONS

The present application is a 35 U.S.C. § 371 U.S. national entry of International Application PCT/US2012/064383 (WO 2013/071059) having an International filing date of Nov. 9, 2012, which claims the benefit of U.S. provisional application 61/558,137, filed Nov. 10, 2011, both of which are incorporated by reference herein in their entirety.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. The government has certain rights in the invention.

TECHNICAL FIELD

The invention is directed towards methods of treating viral infections using salen manganese compounds, wherein such compounds provide protection from oxidative damage.

BACKGROUND OF THE INVENTION

Molecular oxygen is an essential nutrient for nonfacultative aerobic organisms including humans. Oxygen is used in many important ways, namely, as the terminal electronic acceptor in oxidative phosphorylation, in many dioxygenase reactions, including the synthesis of prostaglandins and of vitamin A from carotenoids, in a host of hydroxylase reactions, including the formation and modification of steroid hormones, and in both the activation and the inactivation of xenobiotics, including carcinogens.

The extensive P-450 system uses molecular oxygen in a host of important cellular reactions. In a similar vein, nature employs free radicals in a large variety of enzymic reactions.

Excessive concentrations of various forms of oxygen and of free radicals can have serious adverse effects on living systems, including the peroxidation of membrane lipids, the hydroxylation of nucleic acid bases, and the oxidation of sulfhydryl groups and of other sensitive moieties in proteins. If uncontrolled, mutations and cellular death result.

Biological antioxidants include well-defined enzymes, such as superoxide dismutase, catalase, selenium glutathione peroxidase, and phospholipid hydroperoxide glutathione peroxidase. Nonenzymatic biological antioxidants include tocopherols and tocotrienols, carotenoids, quinones, bilirubin, ascorbic acid, uric acid, and metal-binding proteins. Various antioxidants, being both lipid and water soluble, are found in all parts of cells and tissues, although each specific antioxidant often shows a characteristic distribution pattern. The so-called ovothiols, which are mercaptohistidine derivatives, also decompose peroxides nonenzymatically.

Free radicals, particularly free radicals derived from molecular oxygen, are believed to play a fundamental role in a wide variety of biological phenomena. In fact, it has been suggested that much of what is considered critical illness may involve oxygen radical ("oxyradical") pathophysiology (Zimmermen J J (1991) Chest 100: 189S). Oxyradical injury has been implicated in the pathogenesis of pulmonary oxygen toxicity, adult respiratory distress syndrome (ARDS), bronchopulmonary dysplasia, sepsis syndrome, and a variety of ischemia-reperfusion syndromes, including myocardial infarction, stroke, cardiopulmonary bypass, organ transplantation, necrotizing enterocolitis, acute renal tubular necrosis, and other disease. Oxyradicals can react with proteins, nucleic acids, lipids, and other biological macromolecules producing damage to cells and tissues, particularly in the critically ill patient.

Free radicals can originate from many sources, including aerobic respiration, cytochrome P-450-catalyzed monooxygenation reactions of drugs and xenobiotics (e.g., trichloromethyl radicals, $CCl_3$, formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen creating two radicals H. and .OH. The hydroxyl radical, .OH, is the most reactive radical known in chemistry. It reacts with biomolecules and sets off chain reactions and can interact with the purine or pyrimidine bases of nucleic acids. Indeed, radiation-induced carcinogenesis may be initiated by free radical damage (Breimer L H (1988) Brit. J. Cancer 57: 6). Also for example, the "oxidative burst" of activated neutrophils produces abundant superoxide radical, which is believed to be an essential factor in producing the cytotoxic effect of activated neutrophils. Reperfusion of ischemic tissues also produces large concentrations of oxyradicals, typically superoxide (Gutteridge J M C and Halliwell B (1990) Arch. Biochem. Biophys. 283: 223). Moreover, superoxide may be produced physiologically by endothelial cells for reaction with nitric oxide, a physiological regulator, forming peroxynitrite, $ONOO^-$ which may decay and give rise to hydroxyl radical, .OH (Marletta M A (1989) Trends Biochem. Sci. 14: 488; Moncada et al. (1989) Biochem. Pharmacol. 38: 1709; Saran et al. (1990) Free Rad. Res. Commun. 10: 221; Beckman et al. (1990) Proc. Natl. Acad. Sci. (U.S.A.) 87: 1620). Additional sources of oxyradicals are "leakage" of electrons from disrupted mitochondrial or endoplasmic reticular electron transport chains, prostaglandin synthesis, oxidation of catecholamines, and platelet activation.

Oxygen, though essential for aerobic metabolism, can be converted to poisonous metabolites, such as the superoxide anion and hydrogen peroxide, collectively known as reactive oxygen species (ROS). Increased ROS formation under pathological conditions is believed to cause cellular damage through the action of these highly reactive molecules on proteins, lipids, and DNA. During inflammation, ROS are generated by activated phagocytic leukocytes; for example, during the neutrophil "respiratory burst", superoxide anion is generated by the membrane-bound NADPH oxidase. ROS are also believed to accumulate when tissues are subjected to ischemia followed by reperfusion.

Many free radical reactions are highly damaging to cellular components; they crosslink proteins, mutagenize DNA, and peroxidize lipids. Once formed, free radicals can interact to produce other free radicals and non-radical oxidants such as singlet oxygen ($^1O2$) and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman E R (1992) Science 257: 1220).

SUMMARY OF THE INVENTION

In one aspect, the invention provides a method of treating a disease or disorder associated with viral infection in a subject, the method comprising the step of administering to the subject an effective amount of a compound of formula I, (I)

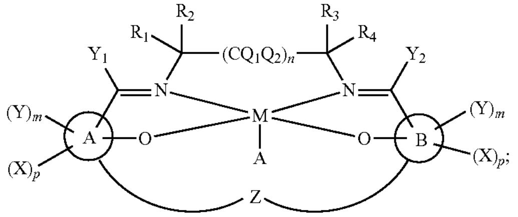

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, ester or hydrate thereof.

In another aspect, the invention provides a method of treating a disease or disorder associated with viral infection in a subject, wherein the subject is identified as being in need of suppression of oxidative stress, the method comprising the step of administering to the subject an effective amount of a compound as described herein (e.g., formula I); or a pharmaceutically acceptable salt, ester or hydrate thereof.

In another aspect, the invention provides a method of treating a disease or disorder associated with viral infection in a subject, wherein the subject is identified as being in need of a scavenger of reactive oxygen species or reactive nitrogen species, the method comprising the step of administering to the subject an effective amount of a compound as described herein (e.g., formula I); or a pharmaceutically acceptable salt, ester or hydrate thereof.

In another aspect, the invention provides a method for the prophylaxis or treatment of a viral infection in a subject, comprising administering to a subject in need of such treatment a therapeutically effective amount of a compound as described herein (e.g., formula I); or a pharmaceutically acceptable salt, ester or hydrate thereof.

In another aspect, the invention provides a method of suppression of oxidative stress in a subject, the method comprising the step of administering to the subject an effective amount of a compound as described herein (e.g., formula I); or a pharmaceutically acceptable salt, ester or hydrate thereof.

In another aspect, the invention provides a method of increasing catalase/superoxide dismutase mimetic activity in a subject, the method comprising the step of administering to the subject an effective amount of a compound as described herein (e.g., formula I); or a pharmaceutically acceptable salt, ester or hydrate thereof.

In another aspect, the invention provides a method of protecting from mitochondrial injury, the method comprising the step of administering to the subject an effective amount of a compound as described herein (e.g., formula I); or a pharmaceutically acceptable salt, ester or hydrate thereof.

DETAILED DESCRIPTION OF THE INVENTION

METHODS OF TREATMENT

Figure 1:
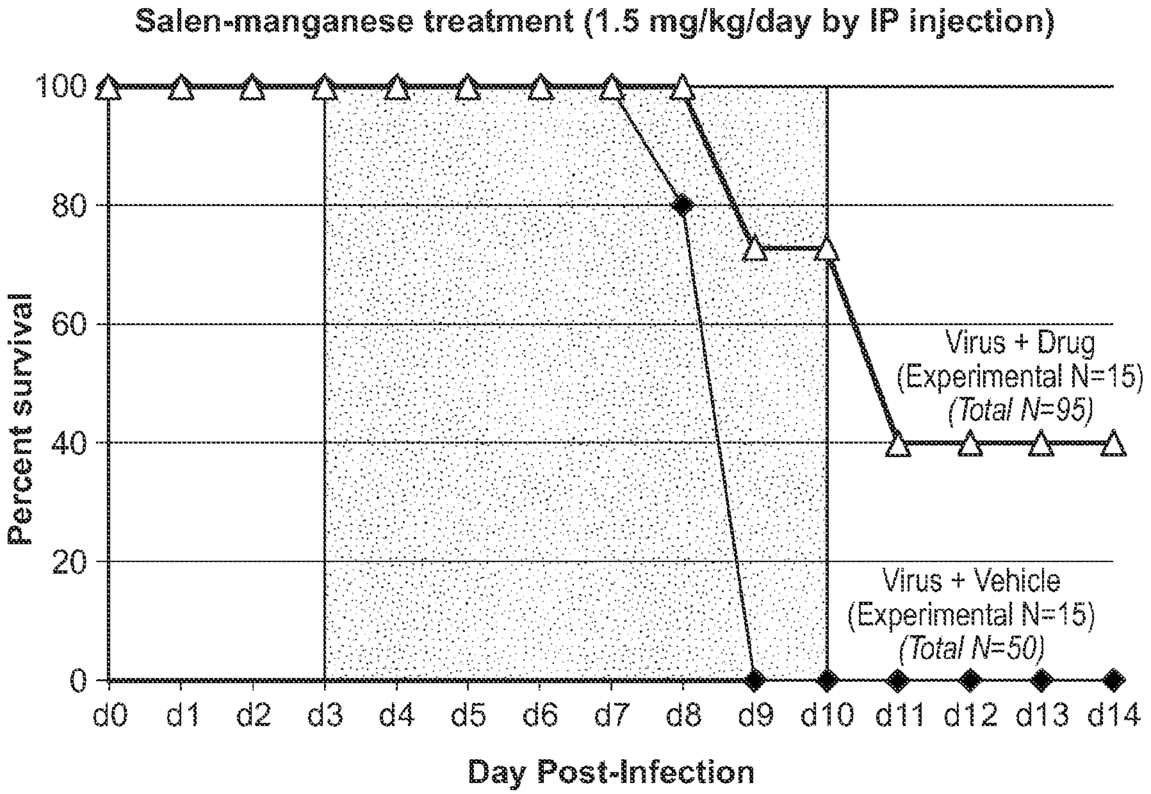
FIG. 1. Mice infected with a lethal dose of the 1918 virus and treated day 3 to 10 post-exposure with the Salen-manganese catalase mimetic EUK-207 showed significantly increased survival and greatly lessened lung pathology compared to vehicle treated controls.

In one aspect, the invention provides a method of treating a disease or disorder associated with viral infection in a subject, the method comprising the step of administering to the subject an effective amount of a compound of formula I, (I)

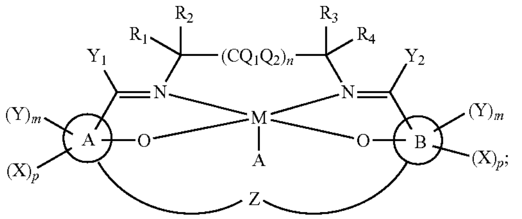

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, ester or hydrate thereof.

In another aspect, the invention provides a method of treating a disease or disorder associated with viral infection in a subject, wherein the subject is identified as being in need of suppression of oxidative stress, the method comprising the step of administering to the subject an effective amount of a compound of formula I, (I)

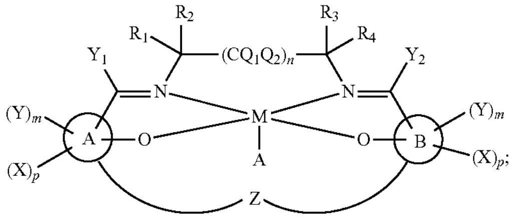

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, ester or hydrate thereof.

In one embodiment, the compound suppresses oxidative stress to thereby treat viral infection.

In another aspect, the invention provides a method of treating a disease or disorder associated with viral infection in a subject, wherein the subject is identified as being in need of a scavenger of reactive oxygen species or reactive nitrogen species, the method comprising the step of administering to the subject an effective amount of a compound of formula I, (I)

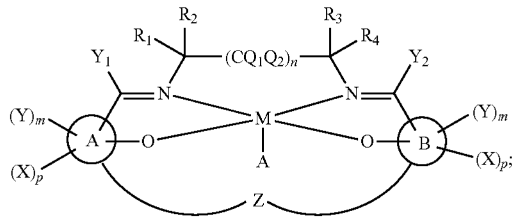

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, $—CN$, $—CF_3$, $—N_3$, $—NO_2$, $—OR_A$, $—SR_A$, $—SOR_A$, $—SO_2R_A$, $—N(R_A)S(O_2)—R_A$, $—N(R_A)S(O_2)NR_AR_B$, $—NR_AR_B$, $—C(O)OR_A$, $—C(O)R_A$, $—C(O)NR_AR_B$, or $—N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, $—CN$, $—CF_3$, $—N_3$, $—NO_2$, $—OR_A$, $—SR_A$, $—SOR_A$, $—SO_2R_A$, $—N(R_A)S(O_2)—R_A$, $—N(R_A)S(O_2)NR_AR_B$, $—NR_AR_B$, $—C(O)OR_A$, $—C(O)R_A$, $—C(O)NR_AR_B$, or $—N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, $—CN$, $—CF_3$, $—N_3$, $—NO_2$, $—OR_A$, $—SR_A$, $—SOR_A$, $—SO_2R_A$, $—N(R_A)S(O_2)—R_A$, $—N(R_A)S(O_2)NR_AR_B$, $—NR_AR_B$, $—C(O)OR_A$, $—C(O)R_A$, $—C(O)NR_AR_B$, or $—N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, $—CN$, $—CF_3$, $—N_3$, $—NO_2$, $—OR_A$, $—SR_A$, $—SOR_A$, $—SO_2R_A$, $—N(R_A)S(O_2)—R_A$, $—N(R_A)S(O_2)NR_AR_B$, $—NR_AR_B$, $—C(O)OR_A$, $—C(O)R_A$, $—C(O)NR_AR_B$, or $—N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, $—CN$, $—CF_3$, $—N_3$, $—NO_2$, $—OR_A$, $—SR_A$, $—SOR_A$, $—SO_2R_A$, $—N(R_A)S(O_2)—R_A$, $—N(R_A)S(O_2)NR_AR_B$, $—NR_AR_B$, $—C(O)OR_A$, $—C(O)R_A$, $—C(O)NR_AR_B$, or $—N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, ester or hydrate thereof.

In one embodiment, the compound scavenges a reactive oxygen species or reactive nitrogen species to thereby treat viral infection.

In various embodiments, the disease or disorder is influenza, pandemic influenza virus, a retrovirus, rhabdovirus, filovirus, hepatitis type A, hepatitis type B, hepatitis type C, varicella, adenovirus, human herpes virus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I (HIV-I), and human immunodeficiency virus type II (HIV-II), any picornaviridae, enteroviruses, caliciviridae, any of the Norwalk group of viruses, togaviruses, alphaviruses, flaviviruses, such as Dengue virus, coronaviruses, rabies virus, Marburg viruses, Ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein-Barr virus, human herpesvirus-6, cercopithecine herpes virus 1 (B virus), varicella zoster virus, orthopox virus, West Nile Virus, avian influenza viruses, or poxviruses.

In a further embodiment, the disease or disorder is influenza, pandemic influenza virus, hepatitis type A, hepatitis type B, hepatitis type C, herpes simplex type I (HSV-I), herpes simplex type II (HSV-II), mumps virus, measles virus, rubella virus, polio virus, Epstein-Barr virus, varicella zoster virus, orthopox virus, human immunodeficiency virus type I (HIV-I), or human immunodeficiency virus type II (HIV-II).

In another further embodiment, the disease or disorder is influenza or pandemic influenza virus.

In other embodiments, the disorder treated is orthopox, selected from variola major and minor, vaccinia, smallpox, cowpox, camelpox and monkeypox.

Additional diseases or disorders that can be treated or prevented by the present invention include, but are not limited to, those caused by influenza virus, human respiratory syncytial virus, pseudorabies virus, pseudorabies virus II, swine rotavirus, swine parvovirus, bovine viral diarrhea virus, Newcastle disease virus, swine flu virus, swine flu virus, foot and mouth disease virus, hog colera virus, swine influenza virus, African swine fever virus, infectious bovine rhinotracheitis virus, infectious laryngotracheitis virus, La Crosse virus, neonatal calf diarrhea virus, Venezuelan equine encephalomyelitis virus, punta toro virus, murine leukemia virus, mouse mammary tumor virus, equine influenza virus or equine herpesvirus, bovine respiratory syncytial virus or bovine parainfluenza virus.

Probably the most common viral infections are those of the upper respiratory airway (i.e., for example, nose, throat, etc.). These infections include sore throat, sinusitis, and the common cold. Influenza is a viral respiratory infection. In small children, viruses also commonly cause croup and inflammation of the windpipe (i.e., for example, laryngotracheobronchitis) or other airways deeper inside the lungs. Respiratory infections are more likely to cause severe symptoms in infants, older people, and people with a lung or heart disorder.

One aspect of the invention is a method for the treatment or prophylaxis of influenza in a patient to reduce or prevent symptoms associated with influenza virus infection. The patient can be human or any other animal susceptible to influenza infection (e.g. domestic animals such as cats and dogs; livestock and farm animals such as horses, cows, pigs, chickens, etc.). Medical care standards are used to determine that that a patient is likely infected with influenza virus or is at risk of exposure to influenza virus. The influenza virus can be an A or B virus. In specific embodiments, the virus is an influenza A virus (e.g. H1N1, H1N2, H2N2, H3N2, H5N1, H7N7, H9N2, etc.).

Some viruses (i.e., for example, rabies virus, West Nile virus, and several different encephalitis viruses) infect the nervous system. Viral infections also develop in the skin, sometimes resulting in warts or other blemishes.

Other common viral infections are caused by herpes viruses. Eight different herpes viruses infect people, including but not limited to, herpes simplex virus type 1, herpes simplex virus type 2, and varicella-zoster virus cause infections that produce blisters on the skin or mucus membranes. Another herpes virus, Epstein-Barr virus, causes infectious mononucleosis. Cytomegalovirus is a cause of serious infections in newborns and in people with a weakened immune system. Cytomegalovirus can also produce symptoms similar to infectious mononucleosis in people with a healthy immune system. Human herpes viruses 6 and 7 cause a childhood infection called roseola infantum. Human herpes virus 8 has been implicated as a cause of cancer (Kaposi's sarcoma) in people with AIDS.

All of the herpes viruses cause lifelong infection because the virus remains within its host cell in a dormant (latent) state. Sometimes the virus reactivates and produces further episodes of disease. Reactivation may occur rapidly or many years after the initial infection.

In addition, the present invention features methods of using compounds of the present invention or pharmaceutically acceptable salts thereof to treat HCV infection. The methods comprise administering to an HCV patient in need thereof an effective amount of a compound of the invention or a pharmaceutically acceptable salt thereof.

Therapeutic methods of the invention can also include the step of identifying that the subject is in need of treatment of diseases or disorders described herein, e.g., identifying that the subject is in need of treatment for a viral infection. The identification can be in the judgment of a subject or a health professional and can be subjective (e.g., opinion) or objective (e.g., measurable by a test or a diagnostic method). Tests for viral infection such as influenza or HIV infection are known in the art and include polymerase chain reaction-based (PCR-based) amplification and detection of viral RNA; Western blot detection of antibodies; agglutination assays for antibodies; ELISA-based detection of antigens; and line immunoassay (LIA). In each of these methods, a sample of biological material, such as blood, plasma, semen, or saliva, is obtained from the subject to be tested. Thus, the methods of the invention can include the step of obtaining a sample of biological material (such as a bodily fluid) from a subject; testing the sample to determine the presence or absence of viral infection such as HIV infection, HIV particles, or HIV nucleic acids; and determining whether the subject is in need of treatment according to the invention.

The methods delineated herein can further include the step of assessing or identifying the effectiveness of the treatment or prevention regimen in the subject by assessing the presence, absence, increase, or decrease of a marker, including a marker or diagnostic measure of a viral infection such as infection, replication, viral load, or expression of an infection marker; preferably this assessment is made relative to a measurement made prior to beginning the therapy. Such assessment methodologies are known in the art and can be performed by commercial diagnostic or medical organizations, laboratories, clinics, hospitals and the like. As described above, the methods can further include the step of taking a sample from the subject and analyzing that sample. The sample can be a sampling of cells, genetic material, tissue, or fluid (e.g., blood, plasma, sputum, etc.) sample. The methods can further include the step of reporting the results of such analyzing to the subject or other health care professional. The method can further include additional steps wherein (such that) the subject is treated for the indicated disease or disease symptom.

In another aspect, the invention provides a method for the prophylaxis or treatment of a viral infection in a subject, comprising administering to a subject in need of such treatment a therapeutically effective amount of a compound of formula I, (I)

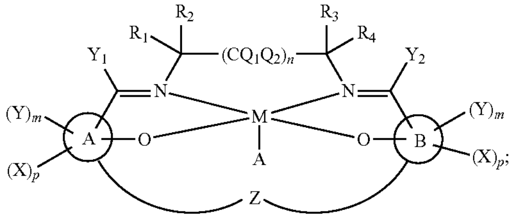

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following:

optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, ester or hydrate thereof.

In certain embodiments, M is a metal, preferably a transition metal. In certain embodiments, M is selected from Mn, Cr, Fe, Zn, Cu, Ni, Co, Ti, V, Ru and Os. In various embodiments, A is an anion. In various embodiments, A is halogen or an organic anion. In a further embodiments, A is $PF_6$, $(Aryl)_4$, $BF_4$, $B(Aryl)_4$, halogen, acetate, acetyl, formyl, formate, triflate, tosylate or, alternatively, A is an oxygen atom typically bound via a double bond to the metal, i.e., M.

In certain embodiments, the invention provides a method as described above, wherein the compound is of formula II, (II)

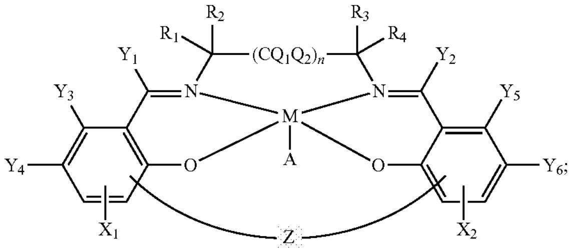

wherein:

M is Mn;

A is halogen, $PF_6$, $(Aryl)_4$, $BF_4$, $B(Aryl)_4$, acetate, acetyl, formyl, formate, propionate, formate, triflate, or tosylate;

$X_1$ and $X_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$, $Y_2$, $Y_3$, $Y_4$, $Y_5$, and $Y_6$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a fused aryl, heteroaryl, cycloalkyl, or heterocycloalkyl;

$Q_1$ and $Q_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein the phenyl rings to which Z is attached are not connected; or Z is —$(R_6)_r$—$(CQ_1Q_2)_q$-$(R_6)_r$—$(CQ_1Q_2)_q$-$(R_6)_r$—;

each $R_6$ is independently O, $NR_x$, $S(O)_t$, alkenyl, alkynyl, aryl, heteroaryl, cyclic, or heterocyclic;

$R_x$ is H or optionally substituted alkyl;

n is 0, 1, or 2;

each q is independently 0, 1, 2, 3, 4, 5, 6, 7, or 8;

each r is independently 0 or 1; and t is 0, 1, or 2;

or a pharmaceutically acceptable salt, ester or hydrate thereof.

In another embodiment, Z is absent wherein the phenyl rings to which Z is attached are not connected.

In other embodiments, Z is $—(CH_2)_q—$, $—(CQ_1Q_2)_q$-, or Z is $—(R_6)_r—(CQ_1Q_2)_q-(R_6)_r—(CQ_1Q_2)_q-(R_6)_r—$; wherein each $R_6$ is independently 0, alkenyl, aryl, or cyclic.

In another embodiment, the invention provides a method as described above, wherein the compound is of formula III, (III)

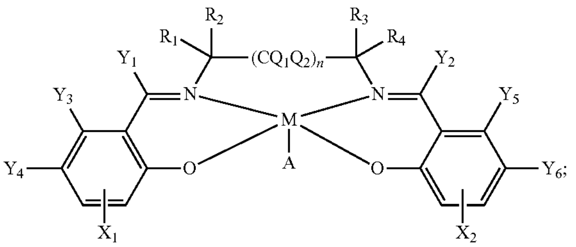

wherein:

M is Mn;

A is halogen, $PF_6$, $(Aryl)_4$, $BF_4$, $B(Aryl)_4$, acetate, acetyl, formyl, formate, propionate, formate, triflate, or tosylate;

$X_1$ and $X_2$ are each independently hydrogen, halogen, alkyl, aryl, heterocyclic, heteroaryl, silyl, fatty acid ester, acyloxy, aralkyl, $—OR_A$, or $—NR_AR_B$; each of which is optionally substituted;

$Y_1$, $Y_2$, $Y_3$, $Y_4$, $Y_5$, and $Y_6$ are each independently hydrogen, halogen, alkyl, aryl, heterocyclic, heteroaryl, silyl, fatty acid ester, acyloxy, aralkyl, $—OR_A$, or $—NR_AR_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, $—OR_A$, $—C(O)OR_A$, $—C(O)R_A$, or $—NR_AR_B$; each of which is optionally substituted; or $R_1$ or $R_2$ may be covalently linked to one of $R_3$ or $R_4$ to form a fused aryl, heteroaryl, cycloalkyl, or heterocycloalkyl;

$Q_1$ and $Q_2$ are each independently hydrogen, halogen, alkyl, aryl, heterocyclic, heteroaryl, silyl, fatty acid ester, acyloxy, aralkyl, $—OR_A$, or $—NR_AR_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and n is 0, 1, or 2;

or a pharmaceutically acceptable salt, ester or hydrate thereof.

In another embodiment, the invention provides a method as described above, wherein the compound is of formula II, (II)

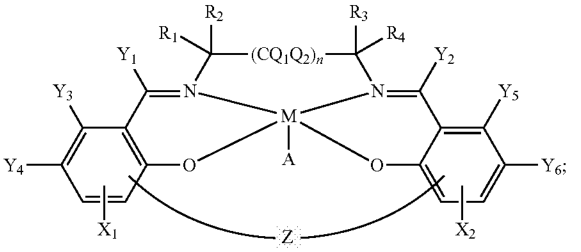

wherein:

M is Mn;

A is halogen, $PF_6$, $(Aryl)_4$, $BF_4$, $B(Aryl)_4$, acetate, acetyl, formyl, formate, propionate, formate, triflate, or tosylate;

$X_1$ and $X_2$ are each independently hydrogen, halogen, alkyl, aryl, heterocyclic, heteroaryl, silyl, fatty acid ester, acyloxy, aralkyl, $—OR_A$, or $—NR_AR_B$; each of which is optionally substituted;

$Y_1$, $Y_2$, $Y_3$, $Y_4$, $Y_5$, and $Y_6$ are each independently hydrogen, halogen, alkyl, aryl, heterocyclic, heteroaryl, silyl, fatty acid ester, acyloxy, aralkyl, $—OR_A$, or $—NR_AR_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, $—OR_A$, $—C(O)OR_A$, $—C(O)R_A$, or $—NR_AR_B$; each of which is optionally substituted; or $R_1$ or $R_2$ may be covalently linked to one of $R_3$ or $R_4$ to form a fused aryl, heteroaryl, cycloalkyl, or heterocycloalkyl;

$Q_1$ and $Q_2$ are each independently hydrogen, halogen, alkyl, aryl, heterocyclic, heteroaryl, silyl, fatty acid ester, acyloxy, aralkyl, $—OR_A$, or $—NR_AR_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is $—(CH_2)_q—$, $—(CQ_1Q_2)_q$-, or $—(R_6)_r—(CQ_1Q_2)_q-(R_6)_r—(CQ_1Q_2)_q-(R_6)_r—$;

each $R_6$ is independently 0, aryl, or cyclic;

n is 0, 1, or 2;

each q is independently 0, 1, 2, 3, 4, 5, 6, 7, or 8; and each r is independently 0 or 1;

or a pharmaceutically acceptable salt, ester or hydrate thereof.

In a further embodiment, $X_1$ and $X_2$ are each independently hydrogen, halogen, alkyl, $—OR_A$, or $—NR_AR_B$; each of which is optionally substituted.

In another embodiment, $X_1$ and $X_2$ are each independently hydrogen or $—OR_A$.

In various embodiments, $Y_1$, $Y_2$, $Y_3$, $Y_4$, $Y_5$, and $Y_6$ are each independently hydrogen, halogen, alkyl, $—OR_A$, or $—NR_AR_B$; each of which is optionally substituted. In a further embodiment, $Y_1$, $Y_2$, $Y_3$, $Y_4$, $Y_5$, and $Y_6$ are each independently hydrogen or halogen. In a further embodiment, $Y_1$, $Y_2$, $Y_3$, $Y_4$, $Y_5$, and $Y_6$ are each independently hydrogen or $—OR_A$. In a further embodiment, $Y_1$, $Y_2$, $Y_3$, $Y_4$, $Y_5$, and $Y_6$ are each independently hydrogen or $—NR_AR_B$.

In other embodiments, n is 0 and $R_1$, $R_2$, $R_3$ and $R_4$ are independently hydrogen, —$OR_A$, or —$NR_AR_B$.

In various embodiments, n is 0 and $R_1$ is covalently linked to $R_3$ or $R_4$ to form a 5 membered or 6 membered fused aryl, heteroaryl, cycloalkyl, or heterocycloalkyl. In a further embodiment, the ring is a cyclohexyl ring, a benzene ring or a pyridine ring.

In certain embodiments, n is 1 and $Q_1$ and $Q_2$ are each independently hydrogen, alkyl, —$OR_A$, or —$NR_AR_B$.

In other embodiments, Z is

—$CH_2.CH_2.O$—$CH_3.CH_2$—; —$CH_2.CH_2.O$—$CH_2.CH_2.O$—$CH_2.CH_2$—;

—$CH_2.O$—$CH_2$—; —$CH_2.CH$=$CH$—$CH_2$—;

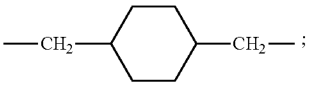

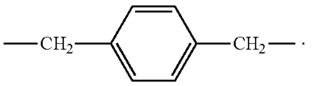

In another embodiments, the invention provides a method as described above, wherein the compound is of formula III:

III

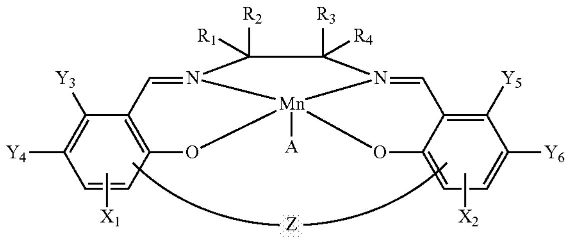

wherein,

A is halogen, $PF_6$, $(Aryl)_4$, $BF_4$, $B(Aryl)_4$, acetate, acetyl, formyl, formate, propionate, formate, triflate, or tosylate;

$X_1$ and $X_2$ are each independently hydrogen, halogen, alkyl, aryl, heterocyclic, heteroaryl, silyl, fatty acid ester, acyloxy, aralkyl, —$OR_A$, or —$NR_AR_B$; each of which is optionally substituted;

$Y_3$, $Y_4$, $Y_5$, and $Y_6$ are each independently hydrogen, halogen, alkyl, aryl, heterocyclic, heteroaryl, silyl, fatty acid ester, acyloxy, aralkyl, —$OR_A$, or —$NR_AR_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —$OR_A$, —$C(O)OR_A$, —$C(O)R_A$, or —$NR_AR_B$; each of which is optionally substituted; or $R_1$ or $R_2$ may be covalently linked to one of $R_3$ or $R_4$ to form a fused aryl, heteroaryl, cycloalkyl, or heterocycloalkyl;

$Q_1$ and $Q_2$ are each independently hydrogen, halogen, alkyl, aryl, heterocyclic, heteroaryl, silyl, fatty acid ester, acyloxy, aralkyl, —$OR_A$, or —$NR_AR_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent; or —$(CH_2)_q$—, —$(CQ_1Q_2)_q$-, or —$(R_6)_r$—$(CQ_1Q_2)_q$-$(R_6)_r$—$(CQ_1Q_2)_q$-$(R_6)_r$—;

each $R_6$ is independently O, aryl, or cyclic;

each q is independently 0, 1, 2, 3, 4, 5, 6, 7, or 8; and each r is independently 0 or 1;

or a pharmaceutically acceptable salt, ester or hydrate thereof.]]

In one embodiment, $R_1$, and $R_3$ are each independently H, phenyl, benzyl, O-benzyl, or —$C(O)OR_A$.

In other embodiments, $R_1$ is covalently linked to $R_3$ or $R_4$ to form a cyclohexyl.

In various embodiments, the compound is selected from

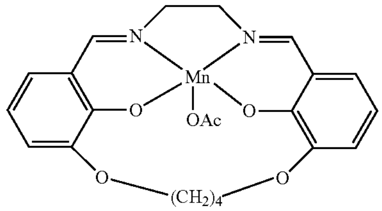

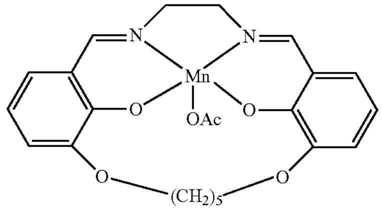

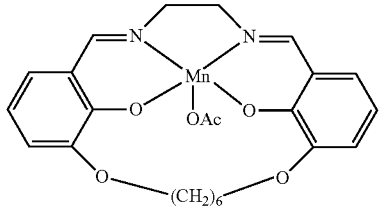

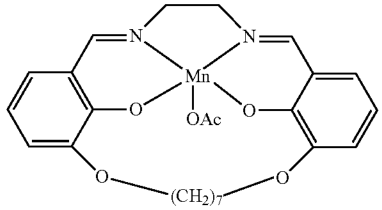

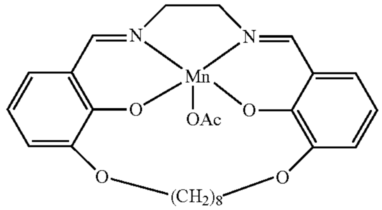

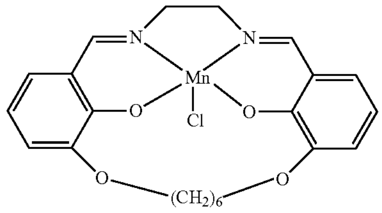

-continued
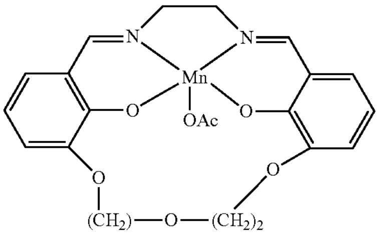
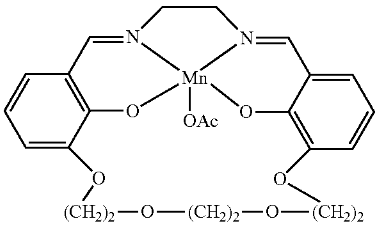
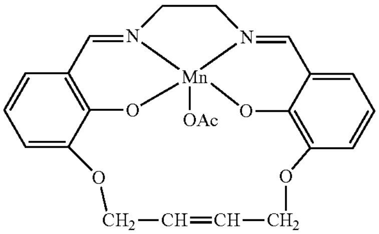
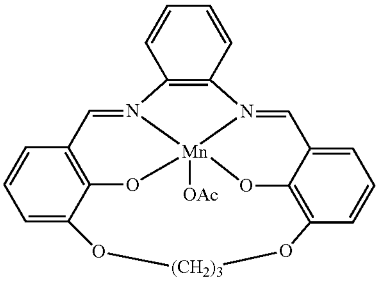
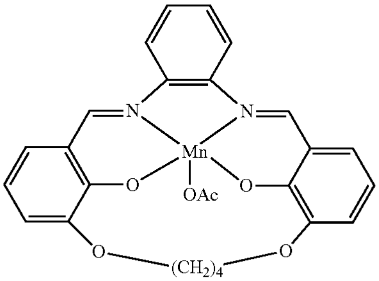
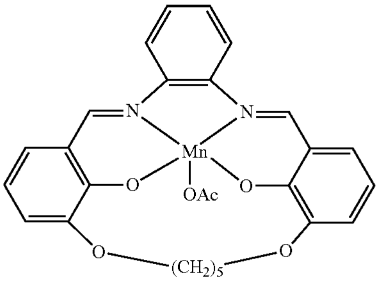
-continued
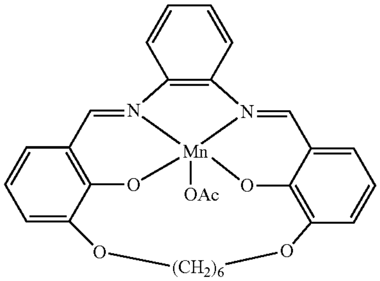
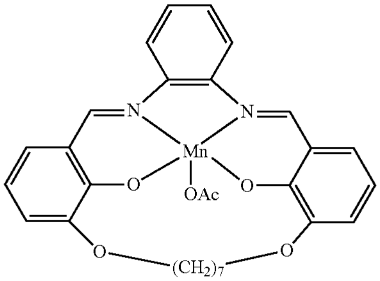
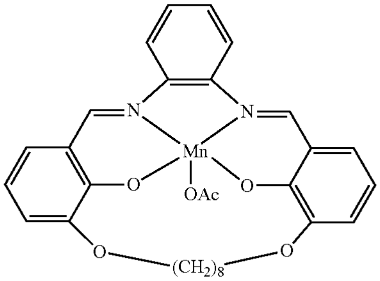
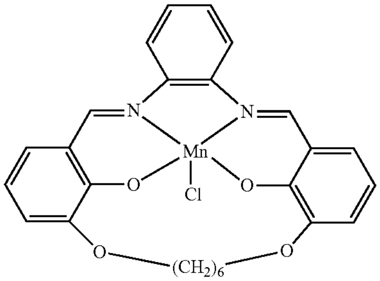
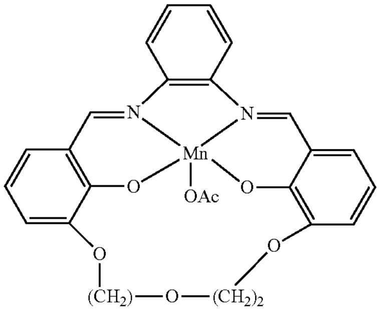
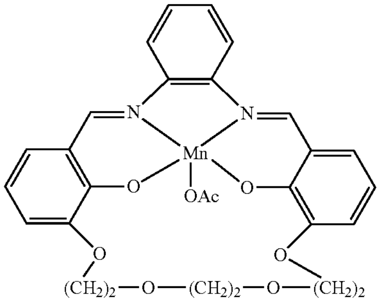

-continued
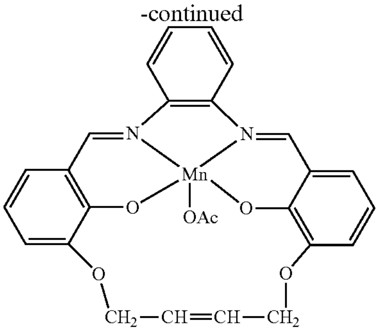
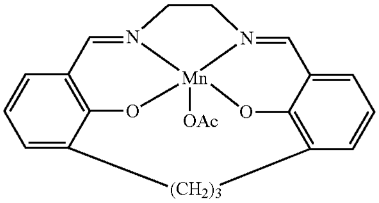
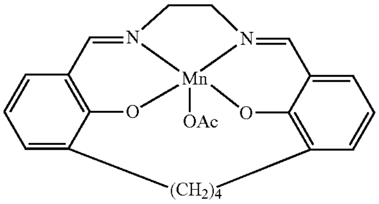
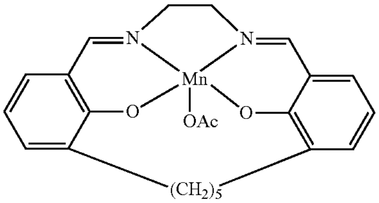
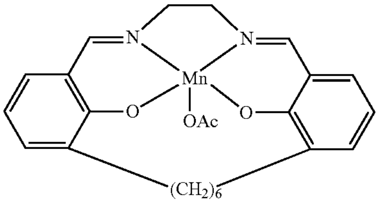
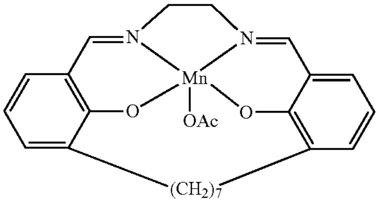
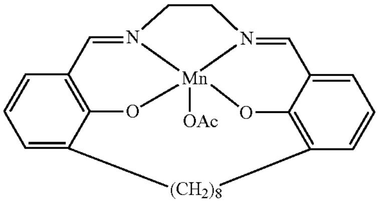
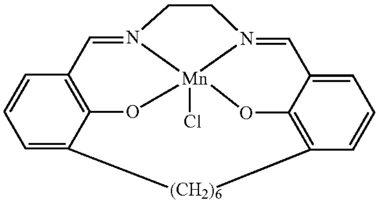
-continued
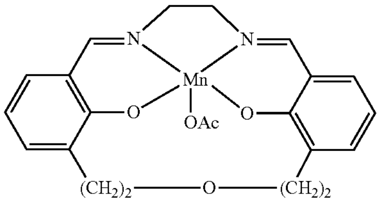
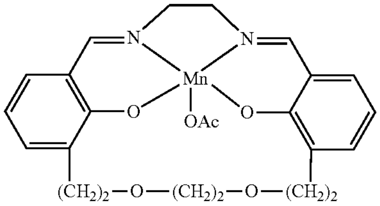
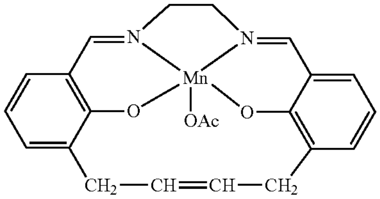
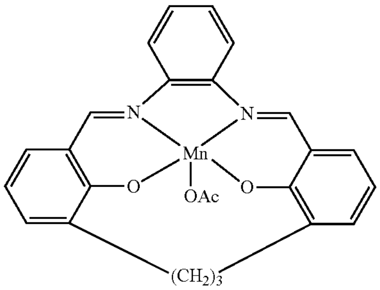
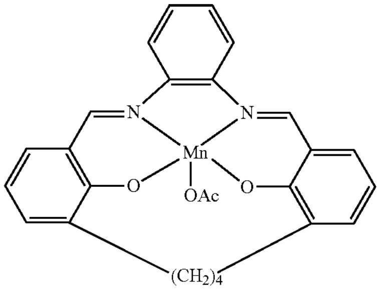
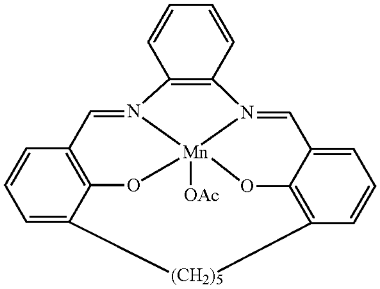

-continued
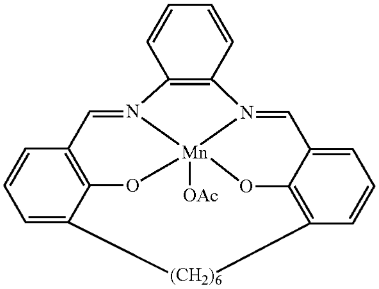
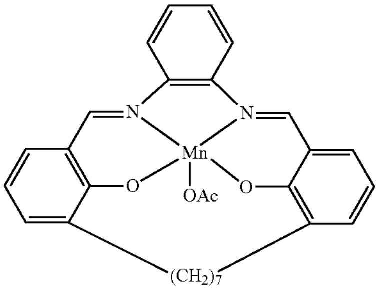
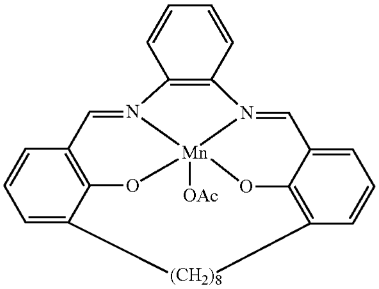
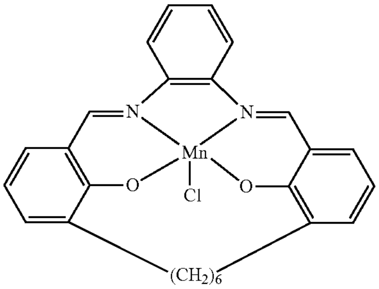
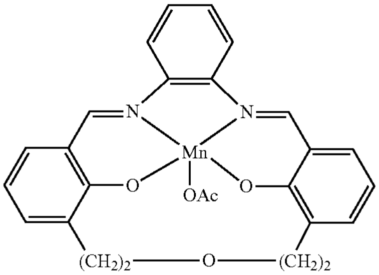
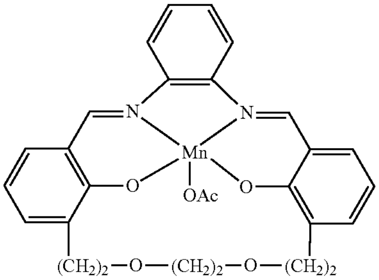
-continued
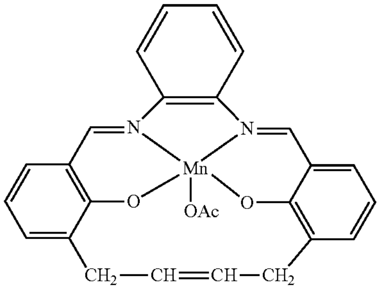
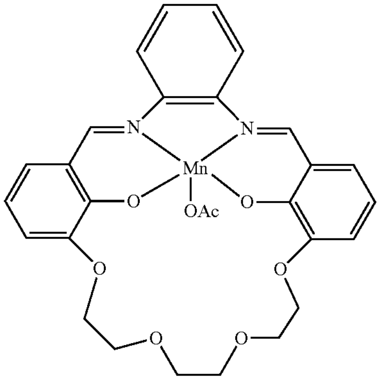
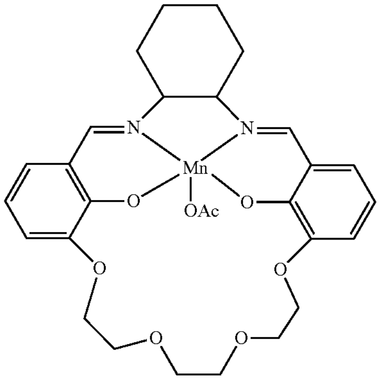
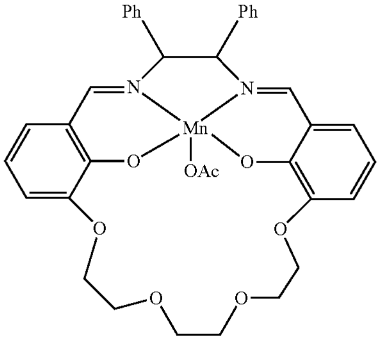
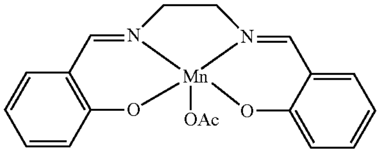
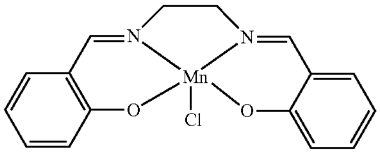

-continued
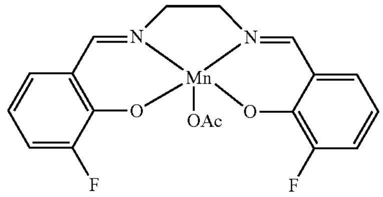
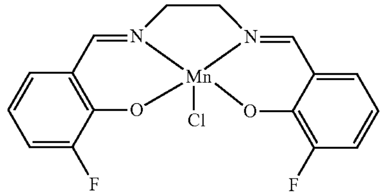
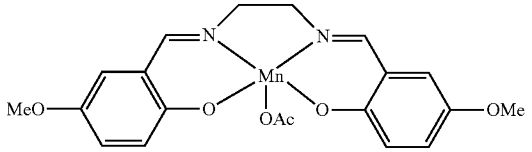
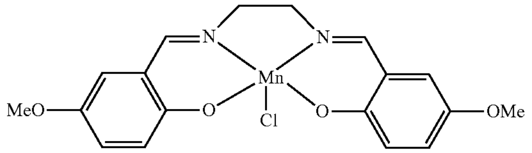
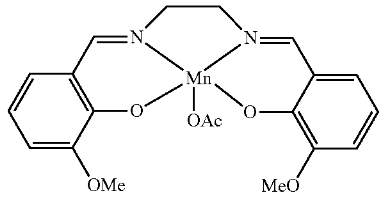
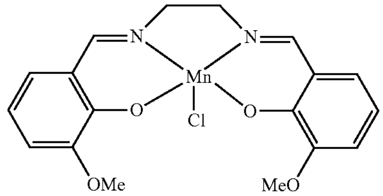
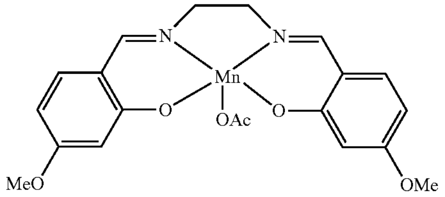
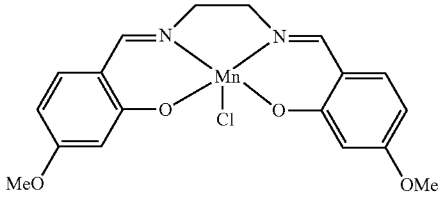
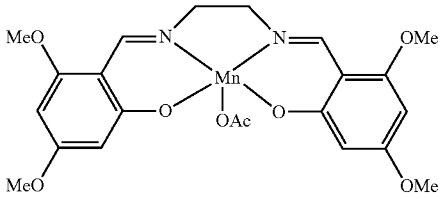
-continued
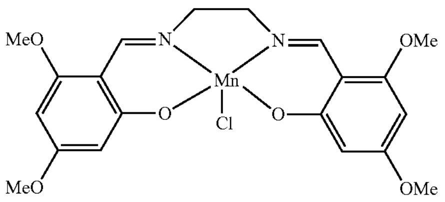
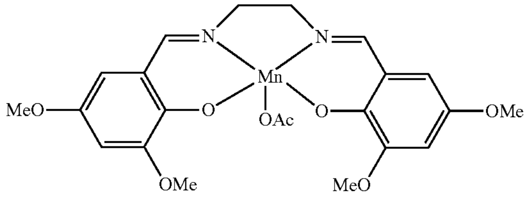
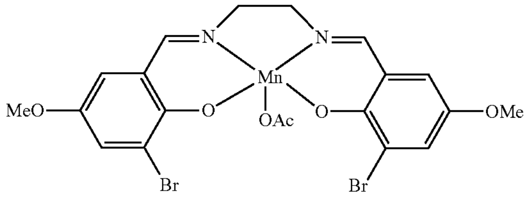
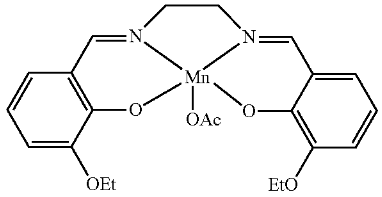
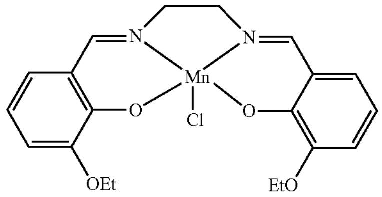
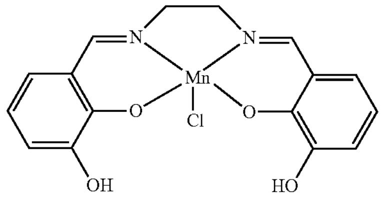
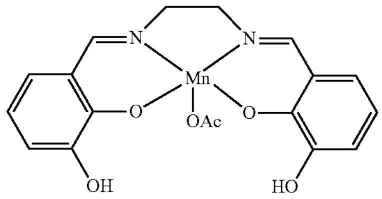
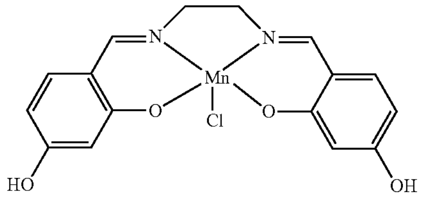

-continued
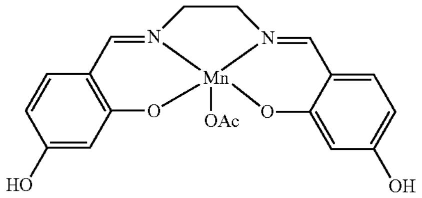
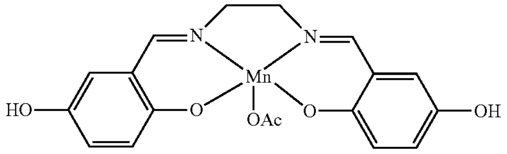
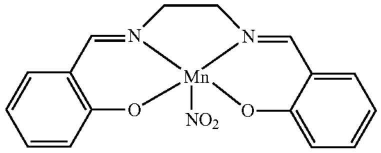
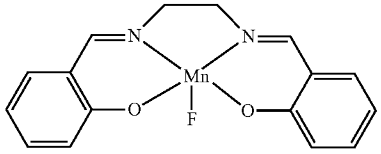
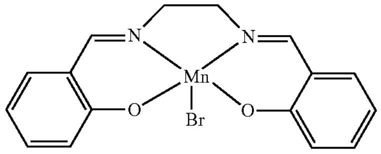
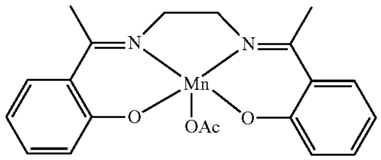
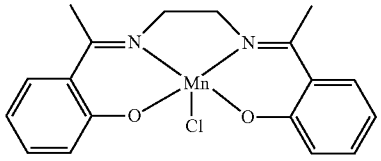
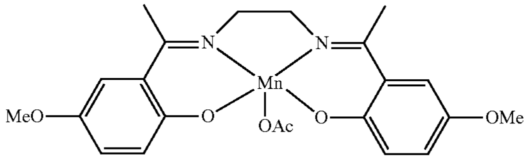
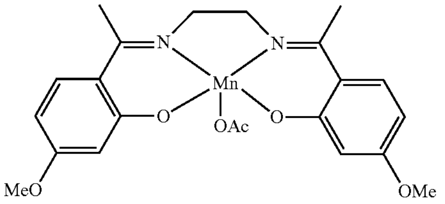
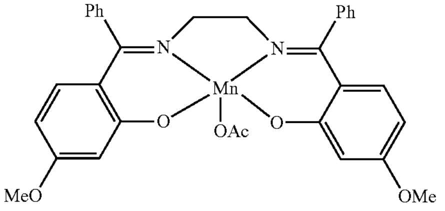
-continued
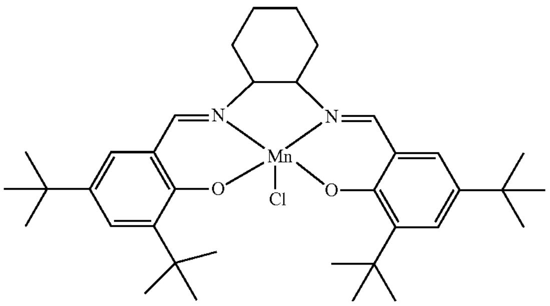
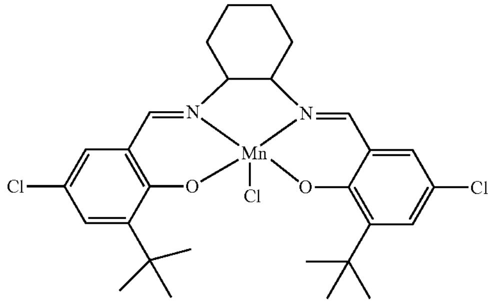
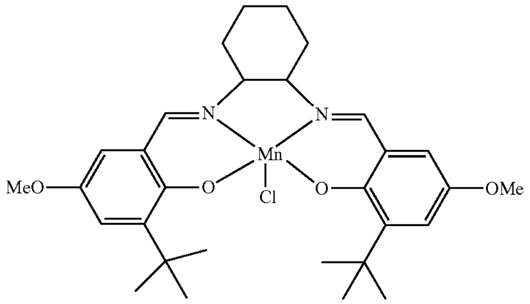
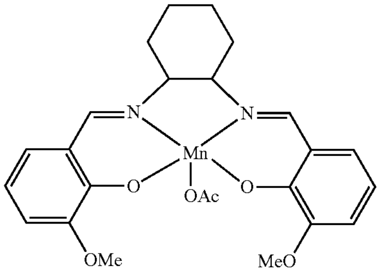
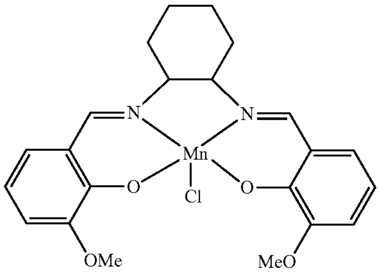
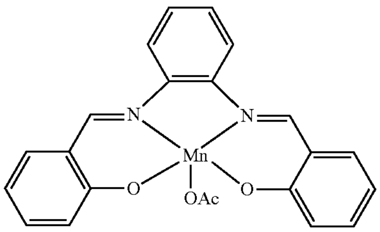

-continued
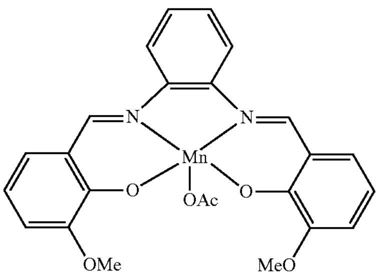
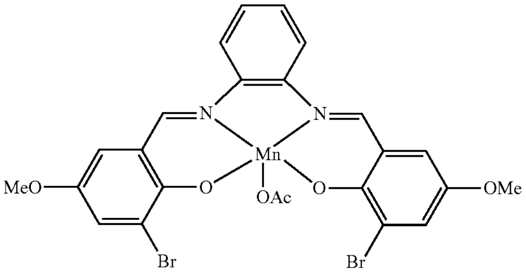
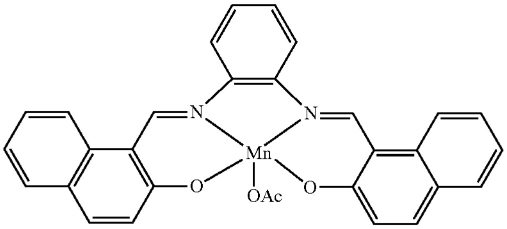
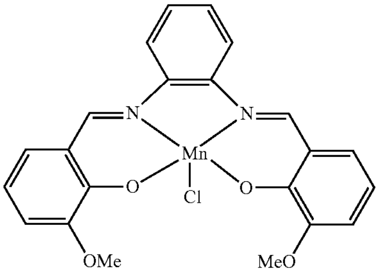
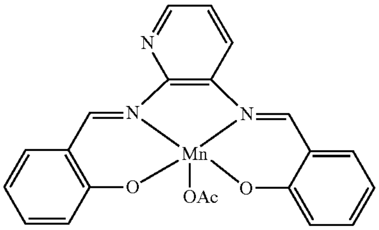
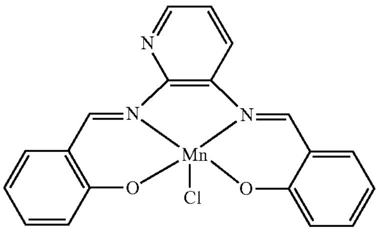
-continued
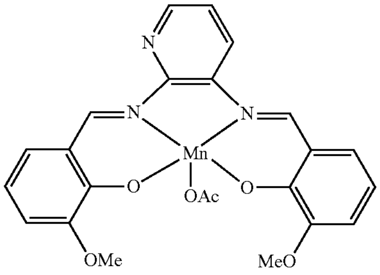
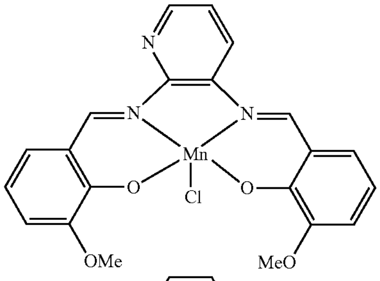
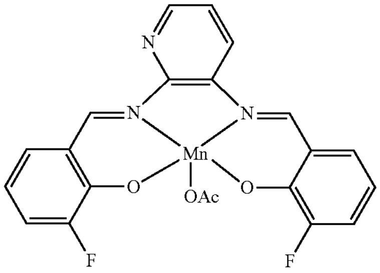
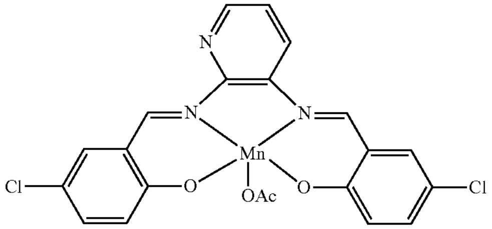
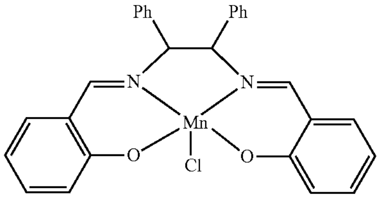
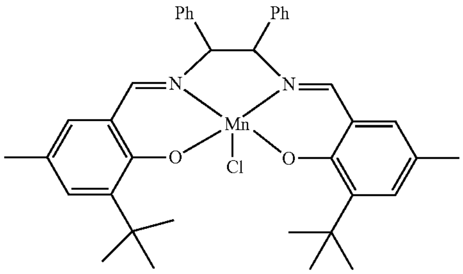
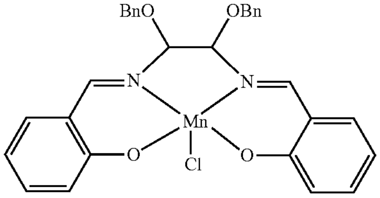

-continued

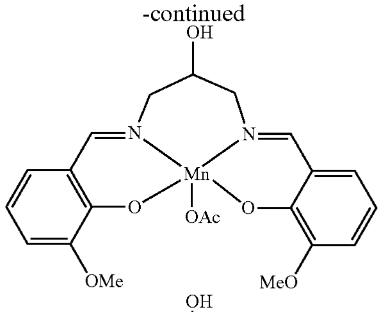

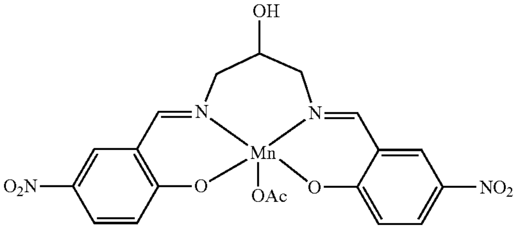

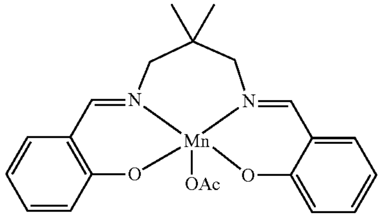

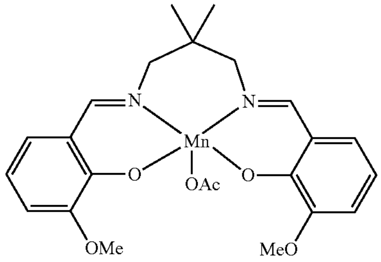

Advantages of the methods of the invention include the low cost of the syntheses of the compounds used, the stability of the compounds, low toxicity, aerosolizable formulation, targets host response pathways, little development of resistance, and broad specificity.

In another aspect, the invention provides a method of suppression of oxidative stress in a subject, the method comprising the step of administering to the subject an effective amount of a compound of formula I, (I)

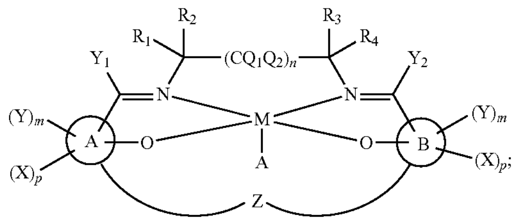

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, ester or hydrate thereof.

In another aspect, the invention provides a method of increasing catalase/superoxide dismutase mimetic activity in a subject, the method comprising the step of administering to the subject an effective amount of a compound of formula I, (I)

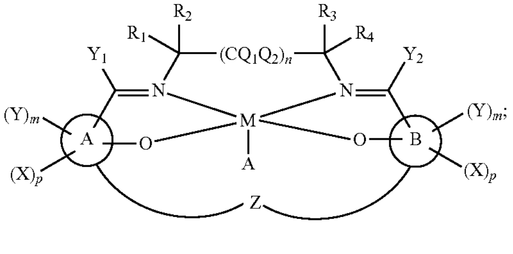

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, ester or hydrate thereof.

In another aspect, the invention provides a method of protecting from mitochondrial injury, the method comprising the step of administering to the subject an effective amount of a compound of formula I,

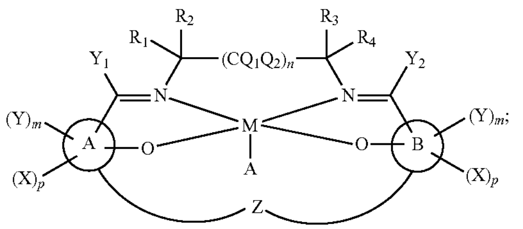

(I)

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, ester or hydrate thereof.

In certain embodiments, the compound is identified in a screening assay.

In a further embodiment, the screening assay is an assay for cell death, an assay for oxidative injury to the mitochondria or other cellular components, an assay for expression of proteins modulated by oxidative stress, or an assay for oxidative post-translational modification of proteins, lipids or nucleic acids In another further embodiment, the compound has a $IC_{50}$ for inhibiting less than about 5 micromolar.

In yet another aspect, the present invention provides methods of using the compounds of the present invention (e.g., formula I) to prevent and/or to treat free radical-associated damage or free radical-associated diseases. More particularly, the present invention provides methods and compositions for the following: (1) preventing ischemic/reoxygenation injury in a patient; (2) preserving organs for transplant; (3) protecting normal tissues from free radical-induced damage consequent to exposure to ionizing radiation (UV light, gamma radiation, etc.) and/or chemotherapy (e.g., with bleomycin); (4) protecting cells and tissues from free radical-induced injury consequent to exposure to xenobiotic compounds that form free radicals, either directly or as a consequence of monooxygenation through the cytochrome P-450 system; (5) enhancing cryopreservation of cells, tissues, organs, and organisms by increasing the viability of recovered specimens; and (6) prophylactic administration to prevent, for example, carcinogenesis, cellular senescence, cataract formation, formation of malondialdehyde adducts, HIV pathology and macromolecular crosslinking, such as collagen crosslinking.

The present invention also provides compounds having peroxidase activity and, therefore, capable of serving as effective peroxidase replacements. These compounds are useful as drugs for the prevention of many pathological conditions, including but not limited to neoplasia, apoptosis of somatic cells, skin aging, cataracts, and the like; and as antioxidants for scavenging $H_2O_2$ and other peroxides. The present invention also provides methods and pharmaceutical compositions of these compounds.

The present invention also concerns a method of reducing $H_2O_2$ and/or other peroxides which comprises contacting $H_2O_2$ and/or other peroxides with a suitable amount of any of the compounds of the invention effective to reduce $H_2O_2$ and/or other peroxides. Additionally, the invention provides a method of treating a peroxide-induced condition in a subject which comprises administering to the subject an amount of any of the compounds of the invention effective to reduce peroxide in a subject and thereby treat the peroxide-induced condition. Further, the invention provides a pharmaceutical composition which comprises an amount of any of the compounds of the invention effective to reduce peroxide in a subject with a peroxide-induced condition and a pharmaceutically acceptable carrier. Further, the invention provides a method of treating a peroxide-induced condition in a subject, e.g. a human subject, which comprises administering, to the subject an amount of a compound described herein (e.g., formula I) effective to reduce peroxide in the subject and thereby treat the peroxide-induced condition. It is worthy to point out at this time that the administration of the compound to the subject may be effected by means other than those listed herein.

Compositions

In another aspect, the invention provides a pharmaceutical composition comprising a therapeutically effective amount of a compound of formula I, (I)

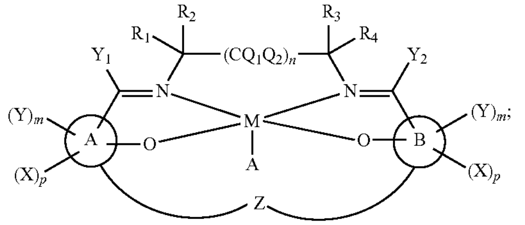

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

or a pharmaceutically acceptable salt, solvate or hydrate thereof, in combination with a pharmaceutically acceptable carrier or excipient.

In one embodiment, the invention provides a pharmaceutical composition, in combination with an anti-viral agent.

In another aspect, the invention provides a method for identifying a protein which has its expression changed by a viral infection, the method comprising:

a) treating a subject with a compound of the invention (e.g., formula I) under conditions suitable for modulation of the amount of the protein; and b) detecting modulation of the amount of the protein after treatment with the compound of the invention (e.g., formula I).

In another aspect, the invention provides a kit comprising an effective amount of a compound of formula I, (I)

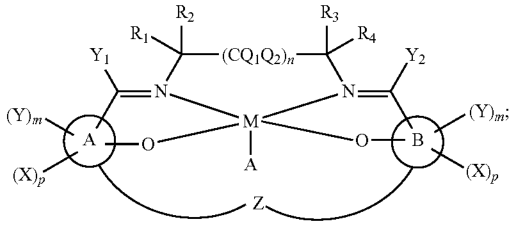

wherein:

M is Mn, Mg, Co, Cu, Zn, V, Cr or Ni;

A is halogen or an organic anion;

ring A and ring B are each independently an aryl or heteroaryl;

each X is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

each Y is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$Y_1$ and $Y_2$ are each independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_1$, $R_2$, $R_3$ and $R_4$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted; or $R_1$ or $R_2$ may be covalently linked to one of $R_3$ or $R_4$ to form a ring;

each $Q_1$ and $Q_2$ are independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following:

optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Z is absent wherein ring A and ring B, to which Z is attached, are not connected; or Z is a bridging group;

n is 0, 1, or 2;

m is 0, 1, or 2; and p is 0 or 1;

in unit dosage form, together with instructions for administering the compound to a subject suffering from or susceptible to a viral disease.

In accordance with the foregoing objects, in one aspect of the invention pharmaceutical compositions are provided which have potent antioxidant and/or free radical scavenging properties and function as in vivo antioxidants. The pharmaceutical compositions of the invention comprise an efficacious dosage of a compound described herein (e.g., formula I). These pharmaceutical compositions possess the activity of dismutating superoxide (i.e., superoxide dismutase activity) and, advantageously, also converting hydrogen peroxide to water (i.e., catalase activity). The pharmaceutical compositions are effective at reducing pathological damage related to formation of oxyradicals such as superoxide and peroxides and other free radical species. In another aspect, the invention provides a pharmaceutical composition comprising a therapeutically effective amount of a compound of the invention (any of the formulae presented herein), or a pharmaceutically acceptable salt, solvate or hydrate thereof thereof, in combination with a pharmaceutically acceptable carrier or excipient.

Yet another aspect of the present invention is a process of making any of the compounds delineated herein employing any of the synthetic means delineated herein. The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or diglycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizating agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Preferably, a compound of the invention is formulated in a solid dispersion, where the compound can be molecularly dispersed in a matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt extrusion, spray drying, or solvent evaporization.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, a disorder is treated in a subject, such as a human or another animal, by administering to the subject a therapeutically effective amount of a compound of the invention (or a pharmaceutically acceptable salt, ester or prodrug thereof), in such amounts and for such time as is necessary to achieve the desired result. The term "therapeutically effective amount" of a compound of the invention, as used herein, means a sufficient amount of the compound so as to decrease the subject's symptoms. As is well understood in the medical arts a therapeutically effective amount of a compound of this invention will be at a reasonable benefit/risk ratio applicable to any medical treatment.

Compounds of the invention also may be administered as a "cocktail" formulation, i.e., coordinated administration of one or more compounds of the invention together with one or more other active therapeutics.

For an antiviral therapy, one or more compounds of the invention including those of Formula I may be administered in coordination with a regime of one or more other antiviral agents such as reverse transcriptase inhibitors such as dideoxynucleosides, e.g. zidovudine (AZT), 2',3'-dideoxyinosine (ddI) and 2',3'-dideoxycytidine (ddC), lamivudine (3TC), stavudine (d4T), and TRIZIVIR (abacavir+zidovudine+lamivudine), nonnucleosides, e.g., efavirenz (DMP-266, DuPont Pharmaceuticals/Bristol Myers Squibb), nevirapine (Boehringer Ingleheim), and delaviridine (Pharmacia-Upjohn), TAT antagonists such as Ro 3-3335 and Ro 24-7429, protease inhibitors, e.g., indinavir (Merck), ritonavir (Abbott), saquinavir (Hoffmann LaRoche), nelfinavir (Agouron Pharmaceuticals), 141 W94 (Glaxo-Wellcome), atazanavir (Bristol Myers Squibb), amprenavir (GlaxoSmithKline), fosamprenavir (GlaxoSmithKline), tipranavir (Boehringer Ingleheim), KALETRA (lopinavir+ritonavir, Abbott), and other agents such as 9-(2-hydroxyethoxymethyl)guanine (acyclovir), interferon, e.g., alpha-interferon, interleukin II, and phosphonoformate (Foscarnet), or entry inhibitors, e.g., T20 (enfuvirtide, Roche/Trimeris) or UK-427,857 (maraviroc, Pfizer). Because many of these drugs are directed to different targets, e.g., viral integration, a synergistic may result with this combination.

In one embodiment, one or more compounds of the invention including those of the formulae herein are used in conjunction with one or more therapeutic agents useful for treatment or prevention of HIV, a symptom associated with HIV infection, or other disease or disease symptom such as a secondary infection or unusual tumor such as herpes, cytomegalovirus, Kaposi's sarcoma and Epstein-Barr virus-related lymphomas among others, that can result in HIV immuno-compromised subjects.

In certain embodiments of the invention, one or more compounds of the invention including those of Formula I are used in conjunction with a standard HIV antiviral treatment regimens. In another aspect, the treatment methods herein include administration of a so-called HIV-drug "cocktail" or combination therapy, wherein a combination of reverse transcriptase inhibitor(s) and HIV protease inhibitor(s) is co-administered.

For antiviral therapies, in a particular aspect, the compounds of the invention can be administered to HIV infected individuals or to individuals at high risk for HIV infection, for example, those having sexual relations with an HIV infected partner, intravenous drug users, etc.

Compounds of the present invention can be administered in combination with one or more agents to treat or prevent influenza a virus, comprising a M2 inhibitor, IMP dehydrogenase inhibitor, RNA polymerase inhibitor, influenza-specific interfering oligonucleotide, and neuraminidase inhibitor.

Preferably each drug in the combination is active at a different phase in the influenza virus life cycle. For example, influenza virus adsorption inhibitors and M2 inhibitors are active at the beginning of the lifecycle; IMP dehydrogenase inhibitors and RNA polymerase inhibitors are active at the middle of the lifecycle; and interfering oligonucleotides and neuramimidase inhibitors are active at the end of the lifecycle.

Examples of M2 inhibitors include aminoadamantane compounds such as amantadine (1-amino-adamantane), rimantadine (1-(1-aminoethyl)adamantane), spiro[cyclopropane-1,2'-adamantan]-2-amine, spiro[pyrrolidine-2,2'-adamantane], spiro[piperidine-2,2'-adamantane], 2-(2-adamantyl)piperidine, 3-(2-adamantyl)pyrrolidine, 2-(1-adamantyl)piperidine, 2-(1-adamantyl)pyrrolidine, and 2-(1-adamantyl)-2-methyl-pyrrolidine; and M2-specific monoclonal antibodies (see e.g. US 20050170334; and Zebedee and Lamb, J. Virol. (1988) 62:2762-72). In a preferred embodiment, one of the antiviral agents in the triple combination is amantadine or rimantadine.

Examples of IMP dehydrogenase inhibitors include ribavirin, viramidine (a prodrug of ribavirin), and merimepodib (VX-497; see e.g. Markland et al., Antimicrob Agents Chemother. (2000) 44:859-66).

The term RNA polymerase inhibitor refers to an antiviral agent that inhibits the polymerase, protease, and/or endonuclease activity of the viral RNA polymerase complex or one of its subunits (i.e. PB1, PB2 and PA). Exemplary RNA polymerase inhibitors include antiviral nucleoside analogs such as ribavirin, viramidine, 6-fluoro-3-hydroxy-2-pyrazinecarboxamide (T-705), 2'-deoxy-2'-fluoroguanosine, pyrazofurin, 3-deazaguanine, carbodine (see e.g. Shannon et al., Antimicrob Agents Chemother. (1981) 20:769-76), and cyclopenenyl cytosine (see e.g. Shigeta et al., Antimicrob Agents Chemother. (1988) 32:906-11); and the endonuclease inhibitor flutimide (see e.g. Tomassini et al., Antimicrob Agents Chemother. (1996) 40:1189-93). In a preferred embodiment, one of the antiviral agents in the triple combination is ribavirin or viramidine.

Examples of influenza-specific interfering oligonucleotides include siRNAs (see e.g. Zhou et al., Antiviral Res. (2007) 76; 186-93), antisense oligonucleotides, phosphorothioate oligonucleotides, ribozymes (see e.g. U.S. Pat. No. 6,258,585 to Draper), morpholino oligomers and peptide nucleic acids (see e.g. Schubert and Kurreck, Handb Exp Pharmacol. (2006) 173:261-87).

Examples of neuraminidase inhibitors include oseltamivir, oseltamivir carboxylate (GS4071; see e.g. Eisenberg et al., Antimicrob Agents Chemother. (1997) 41:1949-52), zanamivir, peramivir (RWJ-27021; BXC-1812, BioCryst), 2,3-didehydro-2-deoxy-N-acetylneuraminic acid (DANA), 2-deoxy-2,3-dehydro-N-trifluoroacetylneuraminic acid (FANA), A-322278, and A-315675 (see U.S. Pat. No. 6,455,571 to Maring et al, and Kati et al., Antimicrob Agents Chemother. (2002) 46:1014-21). In a preferred embodiment, one of the antiviral agents in the triple combination is oseltamivir, peramivir, or zanamivir.

Other agents to be administered in combination with a compound of the present invention include any agent or combination of agents that inhibit the replication of other viruses for co-infected individuals. These agents include but are not limited to therapies for disease caused by hepatitis B (HBV) infection or therapies for disease caused by human immunodeficiency virus (HIV) infection.

In another further embodiment, the other agent or agents are nucleoside HIV reverse transcriptase inhibitors, non-nucleoside HIV reverse transcriptase inhibitors, HIV protease inhibitors, HIV fusion inhibitors, HIV attachment inhibitors, HIV entry inhibitors, CCR5 inhibitors, CXCR4 inhibitors, HIV budding or maturation inhibitors, or HIV integrase inhibitors or combinations thereof.

In various embodiments, the invention provides a method described above wherein the step of administering the compound comprises administering the compound orally, topically, parentally, intravenously or intramuscularly.

In various embodiments, the invention provides a method described above wherein the subject is a human.

The term "inhibitory amount" of a compound of the present invention means a sufficient amount to decrease the viral disorder in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin, which may be intended for administration to a subject. Examples of biological samples include, but are not limited to, blood and components thereof such as plasma, platelets, subpopulations of blood cells and the like;

organs such as kidney, liver, heart, lung, and the like; sperm and ova; bone marrow and components thereof; or stem cells.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

An inhibitory amount or dose of the compounds of the present invention may range from about 0.1 mg/kg to about 500 mg/kg, alternatively from about 1 to about 50 mg/kg. Inhibitory amounts or doses will also vary depending on route of administration, as well as the possibility of co-usage with other agents.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses. For instance a compound of the present invention can be administered to a patient twice a day with a total daily dose of 4000, 4200, 4400, 4600, 4800 or 5000 mg.

In one embodiment, the patient is administered a compound as described above in an amount to maintain a plasma concentration between 0.1 to 10.0 μg/ml, 0.5 to 8 μg/ml, 0.5 to 5.0 μg/ml, 1 to 6 μg/ml, 1 to 4 μg/ml, 2 to 6 μg/ml, 2 to 4 μg/ml, 0.01-2 μg/ml, or 0.2-2 μg/ml for at least 48 continuous hours. In a specific embodiment, the patient is administered a compound as described above in an amount to maintain a plasma concentration between 0.1 to 3.0 μg/ml, 0.1 to 1.5 μg/ml, or 0.3 to 1.5 μg/ml for at least 48 continuous hours.

In another embodiment, the patient is administered a compound as described above parenterally or orally in an amount of 5 to 500 mg/day, 20 to 250 mg/day, 100 to 800 mg/day, 100 to 600 mg/day, 200 to 700 mg/day, or 200 to 500 mg/day. The patient is administered the compound as described above parenterally or orally in an amount of 50 to 2000 mg/day, 50 to 1600 mg/day, 100 to 1200 mg/day, 400 to 800 mg/day, 50 to 600 mg/day, 75 to 500 mg/day, or 75 to 200 mg/day.

In a further embodiment, the patient is administered a compound as described above by intravenous infusion at a rate of 1 to 50 mg/hr, 3 to 40 mg/hr, or 5 to 30 mg/hr for at least 48 continuous hours. In a specific embodiment, the patient is administered the compound as described above by intravenous infusion at a rate of 5 to 200 mg/hr, 10 to 150 mg/hr, 15 to 100, or 20 to 80 mg/hr for at least 48 continuous hours.

In another embodiment, the therapeutically effective amount is from about 0.01 mg to about 5,000 mg per day.

The current method for diagnosis of disease, determining exposure to biological materials such as pathogens, or monitoring immunization status varies depending on the specific assay. Some methods employ an in vivo assay. Others require a biological sample, such as blood or serum, to be obtained and tested. Tests performed usually are one of the non-homogeneous type diagnostic methods such as enzyme-linked immunosorbant assay (hereinafter "ELISA"), radioimmunoassay (hereinafter "RIA"), or agglutination. All are surface-binding, heterogeneous assays and require the antigen of interest to interact with a surface to achieve success, often at the expense of high non-specific binding and loss of specificity.

The embodiments described herein improve upon previously reported immunoassays by providing a totally liquid environment encompassing all steps of the method.

Biological Data

There is great need for the development of novel drug therapies for highly pathogenic influenza virus infections. Drugs that target host response pathways represent a major advance because of the greatly decreased potential for development of antiviral resistance. The 1918 pandemic influenza virus resulted in 40-60 million deaths worldwide.

Studies in animal models have demonstrated that 1918 virus infection results in uncontrolled inflammatory responses hypothesized to lead to immunopathogenic effects, severe lung pathology and lethality. However, no studies have shown that aberrant immune responses are responsible for the extreme pathogenicity of the 1918 influenza virus. Here, it is shown that mice infected with a lethal dose of the 1918 virus and treated day 3 to 10 post-exposure with the Salen-manganese catalase mimetic EUK-207 showed significantly increased survival and greatly lessened lung pathology compared to vehicle treated controls. In three independent studies, mice (n=95 total) infected with a lethal challenge dose of the highly virulent 1918 pandemic influenza virus and treated from day 3 to 10 post-exposure with a Salen-manganese catalase mimetic showed significantly increased survival (40-50%) compared to vehicle alone-treated animals (n=55 total). See FIG. 1. Drug treatment was performed post-exposure by intraperitoneal injection of 1.5 mg/kg/day of EUK-207 diluted in water and given from days 3 to 10 post-infection.

Figure 2:
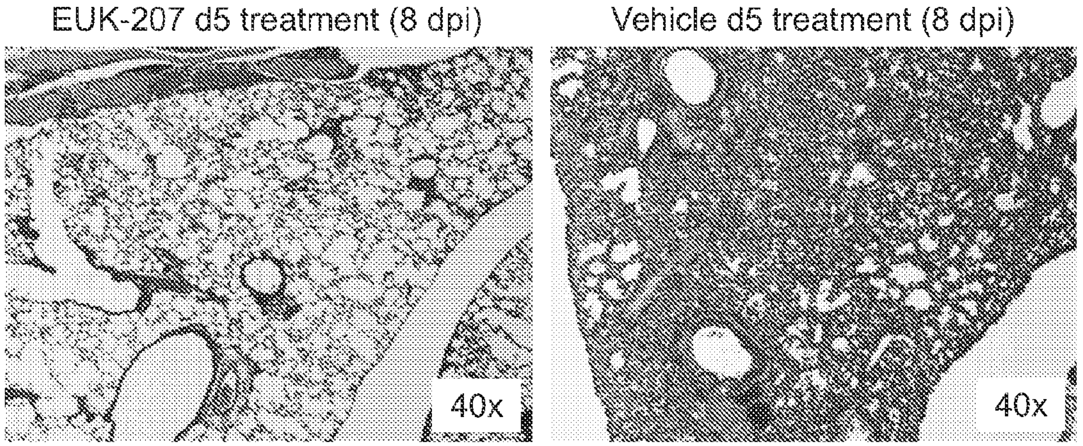
FIG. 2. Salen-manganese treated mice showed greatly lessened lung pathology compared to vehicle treated controls that showed severe necrotizing bronchitis, bronchiolitis, alveolitis, edema and pulmonary hemorrhage.

Salen-manganese treated mice also showed greatly lessened lung pathology compared to vehicle treated controls that showed severe necrotizing bronchitis, bronchiolitis, alveolitis, edema and pulmonary hemorrhage (FIG. 2).

High-throughput next generation RNA sequencing analysis of host lung gene expression showed salen-manganese treatment resulted in a marked decrease in expression of inflammatory response, cell death and cell death related genes, as well as a significant increase in lung repair responses.

Figure 3:
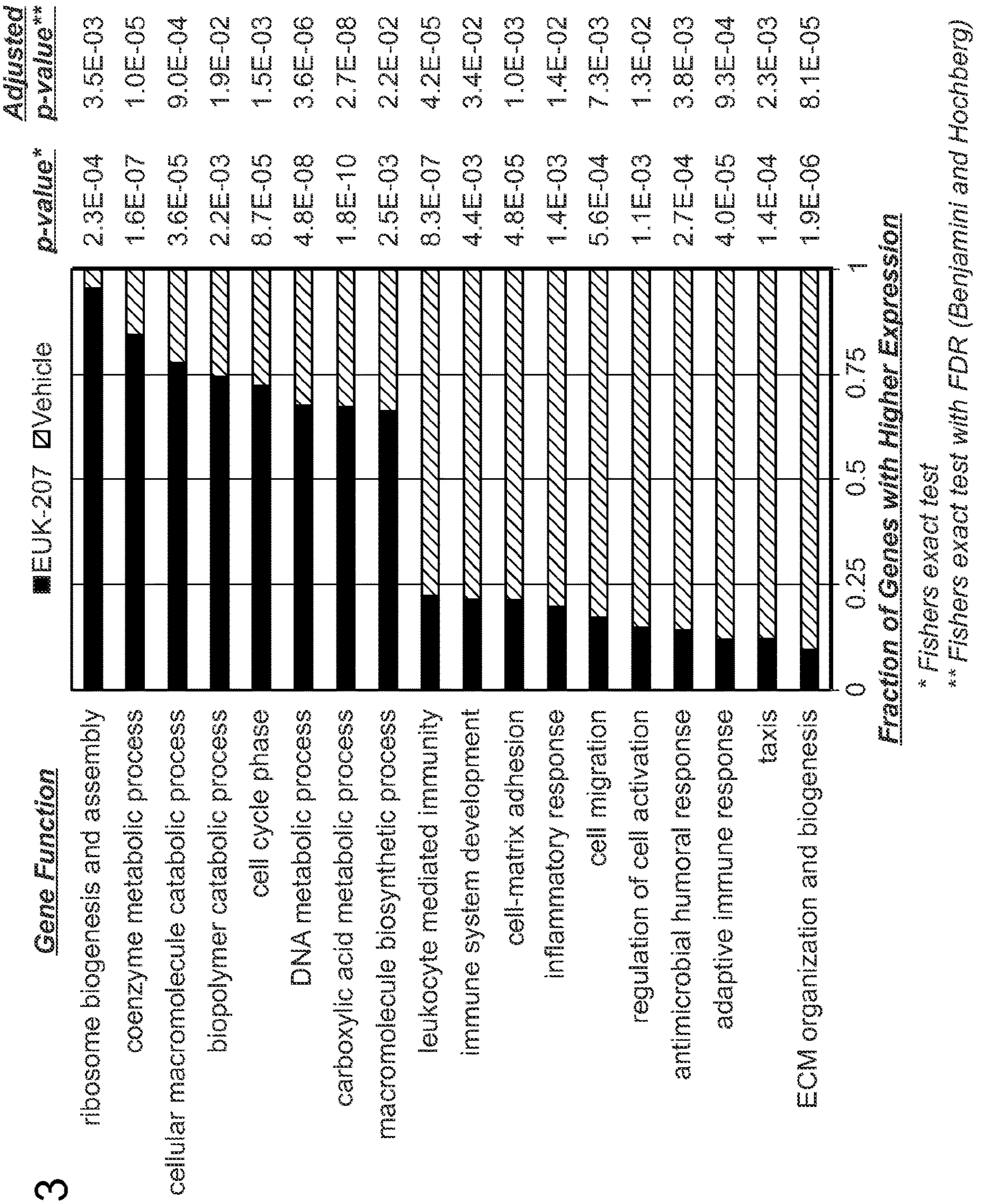
FIG. 3. High coverage viral sequence analysis further showed that salen-manganese drug treatment did not appear to exert any selective pressure on the virus and no changes in the viral genome could be detected demonstrating that drug treatment did not result in generation of resistance mutations.

High coverage viral sequence analysis further showed that salen-manganese drug treatment did not appear to exert any selective pressure on the virus and no changes in the viral genome could be detected demonstrating that drug treatment did not result in generation of resistance mutations (FIG. 3). Our results demonstrate that drugs targeting the host inflammatory response and immune cell killing are efficacious in greatly limiting lung pathology and death during a highly pathogenic influenza viral infection. These results demonstrate that inhibition of reactive oxygen species using salen-manganese compounds produced during highly virulent viral reduces inflammatory and cell death responses; while promoting tissue repair and host survival. Additionally, the use of these compounds to modulate the host inflammatory response are used in the identification of biomarkers associated with both severe disease and survival from infection.

Definitions

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$—$C_y$," where x is the minimum and y is the maximum number of carbon atoms in the substituent. Likewise, a $C_x$ chain means a hydrocarbyl chain containing x carbon atoms.

The term "virus" refers to obligate, ultramicroscopic, intracellular parasites incapable of autonomous replication (i.e., replication requires the use of the host cell's machinery). Viruses are exemplified by, but not limited to, adenovirus, rhinovirus, human papilloma virus, human immunodeficiency virus, hepatitis virus, Newcastle disease virus, cardiovirus, corticoviridae, cystoviridae, epstein-barr virus, filoviridae, hepadnviridae, hepatitis virus, herpes virus, influenza virus, inoviridae, iridoviridae, metapneumovirus, orthomyxoviridae, papovavirus, parainfluenza virus, paramyxoviridae, parvoviridae, polydnaviridae, poxyviridae, reoviridae, respiratory syncytial virus, rhabdoviridae, semliki forest virus, tetraviridae, toroviridae, vaccinia virus, and vesicular stomatitis virus. "Virus" also includes an animal virus that is not a plus-strand RNA virus as exemplified by, but not limited to, Arenaviridae, Baculoviridae, Bimaviridae, Bunyaviridae, Cardiovirus, Corticoviridae, Cystoviridae, Epstein-Ban virus, Filoviridae, Hepadnviridae, Hepatitis virus, Herpesviridae, Influenza virus, Inoviridae, Iridoviridae, Metapneumovirus, Orthomyxoviridae, Papovaviru, Paramyxoviridae, Parvoviridae, Polydnaviridae, Poxyviridae, Reoviridae, Rhabdoviridae, Semliki Forest virus, Tetraviridae, Toroviridae, Vaccinia virus, Vesicular stomatitis virus.

The term "respiratory virus" as used herein, refers to any virus capable of infecting pulmonary tissues (i.e., for example, lung tissue). For example, a respirator virus includes, but is not limited to, influenza, parainfluenza, adenovirus, rhinovirus, herpes simplex virus, respiratory syncytial virus, hantavirus, or cytomegalovirus.

As used herein, "influenza" refers to a contagious respiratory illness or infection caused by a number of viruses. Symptoms of the flu include extreme tiredness, muscle aches, chills, cough, fever, headache, sore throat, runny or stuffy nose, nausea, vomiting, and diarrhea. Influenza viruses are divided into three types, designated A, B, and C. Influenza types A and B are responsible for epidemics of respiratory illness that occur almost every winter and are often associated with increased rates of hospitalization and death. Type C infection usually causes either a very mild respiratory illness or no symptoms at all; it does not cause epidemics and does not have the severe public health impact of influenza types A and B.

As used herein, an "antioxidant" is a substance that, when present in a mixture or structure containing an oxidizable substrate biological molecule, significantly delays or prevents oxidation of the substrate biological molecule. Antioxidants can act by scavenging biologically important reactive free radicals or other reactive oxygen species (e.g., $H_2O_2$, OH, HOCl, ferryl, peroxyl, peroxynitrite, and alkoxyl), or by preventing their formation, or by catalytically converting the free radical or other reactive oxygen species to a less reactive species. An antioxidant salen-transition metal complex of the invention generally has detectable ROS scavenging activity. A salen-transition metal complex of the invention has antioxidant activity if the complex, when added to a cell culture or assay reaction, produces a detectable decrease in the amount of a free radical, such as superoxide, or a nonradical reactive oxygen species, such as hydrogen peroxide, as compared to a parallel cell culture or assay reaction that is not treated with the complex. The relative amount of free radical species is often determined by detection of a secondary indicator (e.g., an oxidized substrate; peroxidized lipid, reduced NBT, cytochrome c). Suitable concentrations (i.e., efficacious dose) can be determined by various methods, including generating an empirical dose-response curve, predicting potency and efficacy of a congener by using QSAR methods or molecular modeling, and other methods used in the pharmaceutical sciences. Since oxidative damage is generally cumulative, there is no minimum threshold level (or dose) with respect to efficacy, although minimum doses for producing a detectable therapeutic or prophylactic effect for particular disease states can be established. Antioxidant salen metal complexes of the invention may have glutathione peroxidase activity or peroxidase activity in general.

As used herein, a "salen-transition metal complex" refers to a compound having a structure according to Formula I or any of the formulae herein. In Formula I, the axial ligand (A) is typically a halogen or an organic anion (such as acetate, propionate, butyrate or formate). The metal (M) is typically a transition metal (such as Mn, Mg, Co, Fe, Cu, Zn, V, Cr, and Ni; preferably Mn or V and, more preferably, Mn; wherein the typical oxidation state is +3).

As used herein, "free radical-associated disease" refers to a pathological condition of an individual that results at least in part from the production of or exposure to free radicals, particularly oxyradicals, and other reactive oxygen species. It is evident to those of skill in the art that most pathological conditions are multifactorial, in that multiple factors contributing to the disease state are present, and that assigning or identifying the predominant causal factor(s) for any individual pathological condition is frequently extremely difficult. For these reasons, the term "free radical associated disease" encompasses pathological states that are recognized in the art as being conditions wherein damage from free radicals or reactive oxygen species is believed to contribute to the pathology of the disease state, or wherein administration of a free radical inhibitor (e.g., desferrioxamine), scavenger (e.g., tocopherol, glutathione), or catalyst (e.g., SOD, catalase) is shown to produce a detectable benefit by decreasing symptoms, increasing survival, or providing other detectable clinical benefits in treating or preventing the pathological state. For example but not limitation, the disease states discussed herein are considered free radical-associated diseases (e.g., ischemic reperfusion injury, inflammatory diseases, systemic lupus erythematosus, myocardial infarction, stroke, traumatic hemorrhage, brain and spinal cord trauma, Crohn's disease, autoimmune diseases (e.g., rheumatoid arthritis, diabeates), cataract formation, uveitis, emphysema, gastric ulcers, oxygen toxicty, neoplasia, undesired cell apoptosis, radiation sickness, and other pathological states disclosed herein, such as toxemia and acute lung injury). Such diseases can include "apoptisus-related ROS," which refers to reactive oxygen species (e.g., $O_2$—, HOOH) which damage critical cellular components (e.g., lipid peroxidation) in cells stimulated to undergo apoptosis, such apoptosis-related ROS may be formed in a cell in response to an apoptotic stimulus and/or produced by non-respiratory electron transpoort chains (i.e., other than ROS produced by oxidative phosphorylation).

As used herein the terms "SOD mimetic," "SOD mimic," "superoxide dismutase mimetic," and "superoxide catalyst" refer to compounds that have detectable catalytic activity for the scavenging of superoxide as determined by assay. Generally, an SOD mimetic possesses at least about 0.001 percent of the SOD activity of human Mn-SOD or Zn, Cu-SOD, on a weight basis, as determined by standard assay methods such as for example the SOD assay used herein below.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein at least one hydrogen radical is replaced with a halogen radical.

If a linking element in a depicted structure is "absent" or "a bond", then the left element in the depicted structure is directly linked to the right element in the depicted structure. For example, if a chemical structure is depicted as X-$(L)_n$-Y wherein L is absent or n is 0, then the chemical structure is X—Y. In certain instances, if a linking element in a depicted structure is "absent", then the left element in the depicted structure is not connected to the right element in the depicted structure. For example, if a chemical structure is depicted as

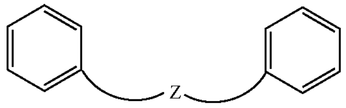

wherein Z is absent, then the chemical structure is one where the left ring and the right ring are not connected.

The term "alkyl" as used herein, refers to a saturated, straight- or branched-chain hydrocarbon radical. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds. For example, "$C_2$-$C_8$ alkynyl" contains from from two to eight carbon atoms. Representative alkynyl groups include, but are not limited to, for example, ethynyl, 1-propynyl, 1-butynyl, heptynyl, octynyl and the like.

The term "cycloalkyl" denotes a monovalent group derived from a monocyclic or polycyclic saturated carbocyclic ring compound. Examples of cycloalkyl include, but not limited to, cyclopropyl, cyclobutyl, cyclopentyl, cyclohexyl, bicyclo[2.2.1]heptyl, and bicyclo[2.2.2]octyl and the like. The terms "carbocycle" or "carbocyclic" or "carbocyclyl" refer to a saturated (e.g., "cycloalkyl"), partially saturated (e.g., "cycloalkenyl" or "cycloalkynyl") or completely unsaturated (e.g., "aryl") ring system containing zero heteroatom ring atom. A carbocyclyl may be, without limitation, a single ring, or two or more fused rings, or bridged or spiro rings. A carbocyclyl may contain, for example, from 3 to 10 ring members (i.e., $C_3$-$C_{10}$-carbocyclyl, such as $C_3$-$C_{10}$cycloalkyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl and the like. A carbocyclyl group can be attached to the parent molecular moiety through any substitutable carbon atom of the group.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heterocycloalkyl" refers to a non-aromatic 3-, 4-, 5-, 6- or 7-membered ring or a bi- or tri-cyclic group fused system, where at least one of the ring atoms is a heteroatom, and where (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocycle" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

-alkyl, -alkenyl, -alkynyl, -aryl, -arylalkyl, -heteroaryl, -heteroarylalkyl, -heterocycloalkyl, -cycloalkyl, -carbocyclic, -heterocyclic, —F, —Cl, —Br, —I, —OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$-heterocycloalkyl, —$NHC(O)NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, $NHC(S)NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —$NHC(NH)NH_2$, —NHC(NH)NH-alkyl, —NHC(NH)NH—-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl —$SO_2NH_2$, —$SO_2$NH-alkyl, —$SO_2$NH-alkenyl, —$SO_2$NH-alkynyl, —$SO_2$NH-cycloalkyl, —$SO_2$NH-aryl, —$SO_2$NH-heteroaryl, —$SO_2$NH-heterocycloalkyl, —$NHSO_2$-alkyl, —$NHSO_2$-alkenyl, —$NHSO_2$-alkynyl, —$NHSO_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$, polyalkoxyalkyl, polyalkoxy, -methoxymethoxy, -methoxyethoxy, —SH, —S—alkyl, —S— alkenyl, —S— alkynyl, —S— cycloalkyl, —S-aryl, —S-heteroaryl, —S-heterocycloalkyl, or methylthiomethyl.

It is understood that the aryls, heteroaryls, carbocycles, heterocycles, alkyls, and the like can be further substituted.

The terms "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "alkylamino" refers to a group having the structure —$N(R_aR_b)$, where $R_a$ and $R_b$ are independent H or alkyl.

The term "silyl" as used herein refers to organometallic substituents, wherein at least one silicon atom is linked to at least one carbon atom; an example of a silyl substituent is the trimethylsilyl substituent, $(CH_3)_3Si$—.

The term "fatty acid ester," as used herein, refers to a substituent that is derived from a fatty acid by removal of a hydrogen. When present, the fatty acid esters typically occupy no more than two substituent positions and are usually identical. Examples of fatty acids from which the fatty acid esters can be derived include palmitoleic, oleic, petroselenic, vaccenic, punicic, parinaric, gadoleic, cetoleic, linoleic, linolenic, arachidonic, lauric, myristic, palmitic, stearic, eicosanoic, and docosanoic.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, "solvate" refers to the physical association of a compound of the invention with one or more solvent molecule, whether organic or inorganic. This physical association often includes hydrogen bonding. In certain instances, the solvate is capable of isolation, for example, when one or more solvate molecules are incorporated in the crystal lattice of the crystalline solid.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)-for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to the schemes as described above, or according to the synthetic steps as described below. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The chemical structures herein contain certain —NH—, —$NH_2$ (amino) and —OH (hydroxyl) groups where the corresponding hydrogen atom(s) may not explicitly appear; however they are to be read as —NH—, —$NH_2$ or —OH as the case may be.

Example 1. Treatment of Viral Infection with Salen Manganese Compounds

Mice were infected with a lethal dose of the 1918 virus and treated day 3 to 10 post-exposure with the Salen-manganese catalase mimetic EUK-207. Drug treatment was performed post-exposure by intraperitoneal injection of 1.5 mg/kg/day of EUK-207 diluted in water and given from days 3 to 10 post-infection. Results are provided in FIG. 1.

Example 2. RNA Isolation and Next Generation Sequencing

Lungs were collected at 8 dpi with influenza and total RNA was isolated from whole mouse lungs of 3 individual mice in each group by homogenization of (10% w/v) in Trizol (Invitrogen) followed by chloroform extraction and isopropanol precipitation. RNA quality was assessed using a BioAnalyzer (Agilent Technologies, CA). Equal amount of total RNA from each mouse were pooled together for experimental or control group. mRNA selection, library preparation and sequencing was performed according to Illumina mRNA-seq sample preparation kit specifications. Briefly, mRNA was selected using oligo(dT) probes and then fragmented using heat treatment. cDNA was synthesized using random primers, modified and enriched for attachment to the Illumina flowcell. The cDNA fragment sizes of the libraries were ~250 bp. We sequenced on two flowcells of 6 lanes each with 36-cycle paired-end runs. Each flowcell contained 3 lanes of EUK treated samples and 3 lanes of vehicle treated samples. In total of 12 lanes, more than 635 million reads of a total of >22 GB of sequence were generated. All three un-filtered paired-end lanes of sequence have been deposited as a series with the accession number GSE #### at NCBI's GEO database. Reads were mapped to bowtie index of mouse genome (UCSC version mm9) downloaded from Center for Bioinformatics and Computational Biology, University of Maryland website (http://bowtie-bio.sourceforge.net/index.shtml) using Tophat (release 1.0.14) (http://tophat.cbcb.umd.edu/) and the published 1918 H1N1 influenza virus genome using a Genomatix Genome Mining Station (Munich, Germany). Overall gene expression level in terms of Reads Per Kilobase per Million mapped reads (RPKM) (reference 2) were calculated by Cufflink package (release 0.8.2) (http://cufflinks.cbcb.umd.edu/). Differential expressed genes between EUK treated and vehicle treated sample were identified by Cuffdiff function from Cufflink package (release 0.8.2) (http://cufflinks.cbcb.umd.edu/). The final set of differential expressed genes was the overlapped data set identified in both runs by Cuffdiff. We used the default options supplied with these software packages in our analyses except for Tophat mapping using -r 250-mate-std-dev 30 and Cufflinks/Cuffdiff calling using -m 250-s 30.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

What is claimed is:

1. A method of treating pandemic influenza viral infection in a subject, the method comprising:

identifying a subject as having a pandemic influenza viral infection that is in need of treatment for at least one of adult respiratory distress syndrome (ARDS), severe necrotizing bronchitis, severe bronchiolitis, severe alveolitis, severe edema, severe pulmonary hemorrhage, or combinations thereof; and administering to the subject an effective amount of a compound, wherein the compound is:

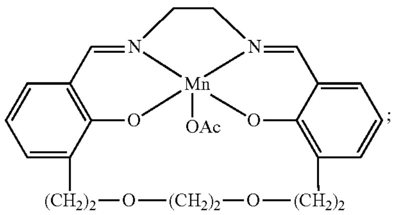

;

or a pharmaceutically acceptable salt, ester or hydrate thereof, wherein the compound is effective at decreasing or reducing at least one symptom of at least one of ARDS, severe necrotizing bronchitis, the severe bronchiolitis, the severe alveolitis, the severe edema, the severe pulmonary hemorrhage, or combinations thereof.

2. The method of claim 1, wherein the compound suppresses oxidative stress to thereby treat viral infection.

3. The method of claim 1, wherein the compound is administered intraperitoneally.

4. The method of claim 1, wherein the pandemic influenza viral infection is an H1N1 influenza viral infection, an H1N2 influenza viral infection, an H2N2 influenza viral infection, an H5N1 influenza viral infection, an H7N7 influenza viral infection, or an H9N2 influenza viral infection.

5. The method of claim 4, wherein the H1N1 influenza viral infection is a 1918 pandemic influenza viral infection.

6. The method of claim 1, wherein the compound is orally administered.

7. A method of treating pandemic influenza viral infection in a subject, the method comprising:

identifying a subject as infected with an H1N1 influenza virus, an H1N2 influenza virus, an H2N2 influenza virus, an H5N1 influenza virus, an H7N7 influenza virus, or an H9N2 influenza virus; and administering to the subject an effective amount of a compound, wherein the compound is:

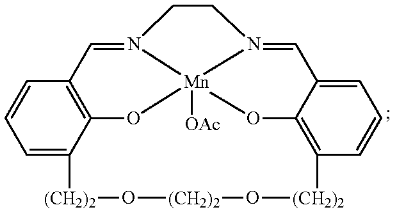

;

or a pharmaceutically acceptable salt, ester or hydrate thereof, wherein the compound effectuates at least one of reduced lung pathology, decreased expression of pro-inflammatory response genes, increased expression of cellular repair genes, prolonged survival or a combination thereof.

8. The method of claim 7, wherein the H1N1 influenza virus is a 1918 pandemic influenza virus.

9. The method of claim 4, wherein the compound is orally administered.

* * * * *